(12) United States Patent
Katz et al.

(10) Patent No.: US 6,681,132 B1
(45) Date of Patent: Jan. 20, 2004

(54) SODIUM MAGNETIC REASONANCE IMAGING USED IN DIAGNOSING TUMORS AND ASSESSING RESPONSE TO TREATMENT

(75) Inventors: Jose Katz, Closter, NJ (US); Richard Paul Kline, Riverdale, NY (US); Edward X. Wu, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/317,068

(22) Filed: May 13, 1999

(51) Int. Cl.7 .............................................. A61B 5/055

(52) U.S. Cl. .......................... 600/410; 436/63; 436/64; 436/173; 324/307; 424/9.2

(58) Field of Search ........................... 600/410; 436/63, 436/64, 173; 324/307, 309; 424/9.2

(56) References Cited

U.S. PATENT DOCUMENTS

| | | |
|---|---|---|
| 5,647,361 A | 7/1997 | Damadian |
| 5,818,230 A | 10/1998 | Katz et al. |
| 6,023,634 A | 2/2000 | Hanawa et al. |

OTHER PUBLICATIONS

Adams, D.A., et al. (1985) "Radioimmunotheraphy of human lymphoma in athymic, nude mice as monitored by $^{31}$P nuclear magnetic resonance", *Biochem & Biophys Res Commun* 131(2):1020–1027.

Allis, J.L., et al. (1991) "Absolute qualification of intracellular Na= using triple quantum–filtered sodium–23 NMR", *J Mag Reson*, 93:71–76.

Balschi, J.A., et al. (1982) "Direct high–resolution nuclear magnetic resonance studies of cation transport in vivo: Na+ transport in yeast cells", *Biophys J*, 38:323–3276.

Bansal, G., et al. (1992) "In vivo Na–23 MR imaging and spectroscopy of rat brain during Tm(DOTP)5–infusion", *J Magn Reson Imag*, 4:385–391.

Berendsen, H.J.C. and Edzes, H.T. (1973) "The observation and general interpretation of sodium magnetic resonance in biological material", *Ann NY Acad Sci*, 104:455–585.

Buster, D.C., et al. (1990) "23Na shift reagent for perfused rat hearts", *Magn Reson Med*, 15:25–32.

Butwell, N.B. et al. (1991) "Influence of cardiac pacing on intracellular sodium in the isolated perfused rat heart", *Invest Radiol*, 26:1079–1082.

Columbano, A. (1995) "Cell Death: current difficulties in discriminating apoptosis from necrosis in the context of pathological processes in vivo", *J Cell Biochem*, 58:181–190.

Cockman, M.D., et al. (1990) "Double–quantum–filtered sodium imaging", *J Magn Reson*, 90:9–18.

Dizon,J., et al. (1996) "Evaluation of triple–quantum filtered Na NMR monitoring of intracellular Na content in the perfused rat heart: Comparison of intra– and extracellular transverse relaxation and spectral amplitudes", *Magn Reson Med*, 35:336.

Elledge, S.J. (1996) "Checkpoints: preventing an identity crisis", *Science*, 274:1664–1671.

Jelicks, L.A. and Gupta, R.K. (1989) "Observation of intracellular sodium ions by double–quantum filtered 23Na NMR with paramagnetic quenching of extracellular coherence by gadolinium tripolyphosphate", *J Magn Reson*, 83:146–151.

Jelicks, L.A. and Gupta, R.K. (1989), "Double–quantum NMR of sodium ions in cells and tissues. Paramagnetic quenching of extracellular coherence", *J Magn Reson*, 81:586–592.

Jelicks, L.A. and Gupta, R.K. (1994) "Nuclear magnetic resonance measurement of intracellular sodium in the perfused normotensive and spontaneously hypertensive rat heart", *Am J Hypertension*, 7:429–435.

Jung, K.J., et al. (1996) "New double quantum filtering schemes", *J. Magn. Reson B.*, 112:103–110.

Jung, K.J., et al. (1996) "Chemical–shift–selective (CSS)acquisition of multiple–quantum (MQ) 23Na signal", *J Mag Reson*, 112:214–227.

Jung, K.J., et al. (1995) "Breakthrough of single–quantum coherence and its elimination in double–quantum filtering", *Magn Reson*, 107: 235–241.

Jung, K.J. and Katz, J. (1996) "Mathematical analysis of single–quantum breakthrough due to intersequence stimulated echo in double quantum filtering (DQF)", *J Magn Reson*, 124:232–236.

Jung, K.J., et al. (1997) "Measurement of transverse relaxation times and content ratio of 23Na in phantoms simulating biological systems by use of multiple–quantum filtering", *J Magn Reson*, 124:393–399.

Karczmar, G.S., et al. (1991) "P–31 spectroscopy study of response of superficial human tumors to therapy", *Radiology*, 179:149–153.

King, K.L. and Cidlowski, J.A. (1995) "Cell cycle and apoptosis:common pathways to life and death", *J Cell Biochem*, 58:175–180.

(List continued on next page.)

*Primary Examiner*—Ruth S. Smith
(74) *Attorney, Agent, or Firm*—John P. White; Cooper & Dunham LLP

(57) ABSTRACT

The present invention provides a method for measuring the magnetic resonance signal of an intracellular population of predetermined nuclei in a cell-containing sample by: a) applying to the sample a first radio frequency pulse, in a magnetic field, b) after a set time interval ($T_l$), applying to the sample a second radio frequency pulse sufficient to cause a measurable signal, and c) measuring the measurable signal for the sample so produced, which method is utilized in methods of (i) determining the effectiveness of chemotherapy, (ii) detecting and characterizing tumors, and (iii) determining cell death in a cell-containing sample.

37 Claims, 17 Drawing Sheets

OTHER PUBLICATIONS

Koutcher, J.A., et al., (1990) "P–31 NMR spectra of extremity sarcomas: diversity of metabolic profiles and changes in response to chemotherapy", *Magn Reson Med,* 16:19–34.

Liebling, M.S. and Gupta, R.K. (1987) "A comparison of intracellular sodium ion concentrations in neoplastic and nonneoplastic human tissue using 23Na NMR spectroscopy", *Ann NY Acad Sci,* 508:149–163.

Malloy, C.R., et al. (1990) "Influence of global ischemia on intracellular sodium in the perfused rat heart"*Magn Reson Med,* 15:33–44.

Miller, J.R., et al. (1996) "High temperature superconducting receiver coils for sodium imaging", *IEE Trans on Biomed Engineering Reson,* 43:1197–1199.

Navon, G. (1993) "Complete elimination of the 23Na NMR signal in triple quantum filtered spectra of rat hearts in the presence of shift reagents", *Magn Reson Med,* 30:503.

Payne, G.S. and Styles, P. (1991) "Multiple–quantum filtered 23 Na NMR spectroscopy in model systems", *J Magn Reson,* 95:253–266.

Pekar, J., et al. (1987) "selective detection of intracellular sodium by coherence–transfer NMR", *J Magn Reson,* 72:159–161.

Redmon, O.M., et al. (1992) "Osteosarcoma: use of MR imaging and MR spectroscopy in clinical decision making", *Radiology,* 172:811–815.

Redmon, O.M., et al. (1992) "P–31 MRS as an early prognostic indicator of patient response to chemotheraphy", *Magn Reson Med,* 25:30–44.

Redmon, O.M., et al. (1992) "Tissue characterization and assessment of preoperative chemotherapeutic response musculoskeletal tumors by in vivo P–31 magnetic resonance spectroscopy", *Magn Reson Med,* 27:226–237.

Rick, R. (1989) "Electron microprobe analysis of cell sodium in epithelia", *Curr Top Membr,* 34:61–82.

Rooney, W.D., et al. (1988) "Two dimensional double–quantum NMR spectroscopy of isolated spin 3/2 systems: 23Na examples",*J Am Chem Soc,* 110:674–681.

Seo, Y., et al. (1990) "Measurement of intracellular Na in the rat salivary gland: a 23Na NMR study using double–quantum filtering", *Biochem Biophys Acta,* 1034:142–147.

Shinar, H., et al. (1993) "Sodium interaction with ordered structures in mammalian red blood cells detected by Na–23 double–quantum NMR", *Biophys J,* 64:1273–1279.

Sorce, D.J. and Katz, J. (1991) "Multiple–quantum filters of arbitrary phases for spin 3/2 nuclei", *Mol Phys,* 80(5):1067–1076.

Tauskela, J.S., et al. (1995) "Detection of an extracellular contribution from a second–rank tensor to the double–quantum 23Na NMR signal in the isolated perfused rat heart",*J Magn Reson,* 108:165–169.

Whang, J., et al. (1994) "Multiple–quantum filtered NMR determination of equilibrium magnetization for 23Na quantitation in model phantoms",*J Magn Reson B,* 103:175–179.

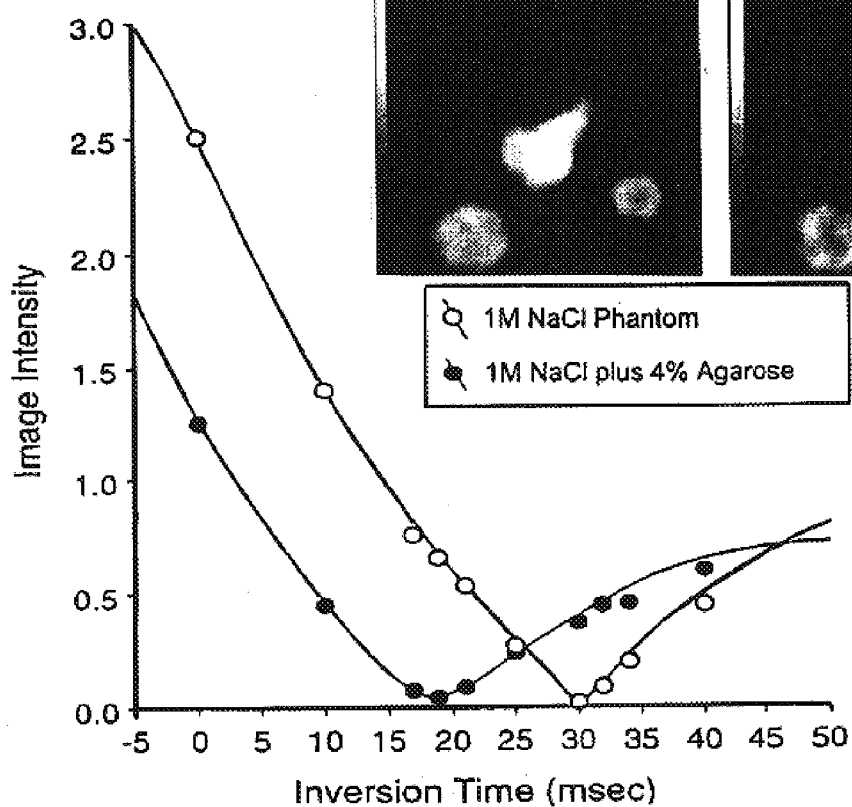
Figure 1, Theoretical Graph of Intensity Response to Inversion Pulse Timing No Inversion TI = 35 ms TI = 25 ms TI = 15 ms Single Quantum  Inversion Recovery

*Comparison of Tumor Intensity : Single Quantum vs. Inversion Recovery*

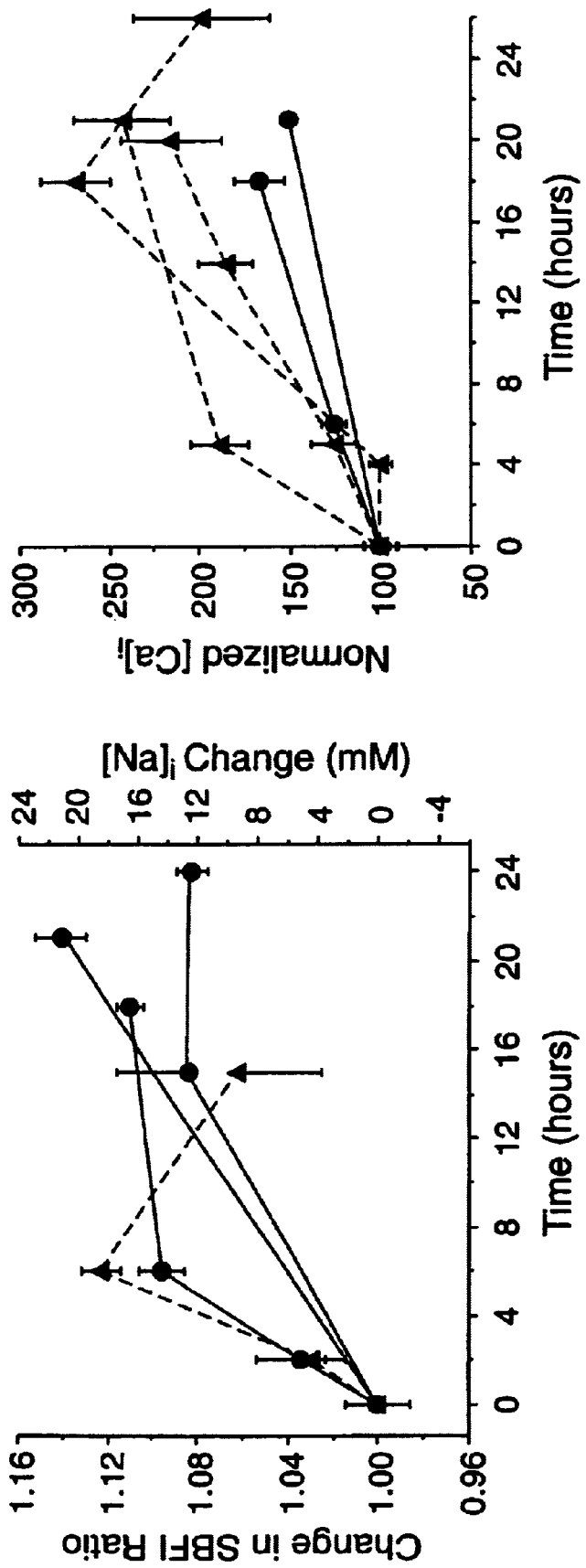

*Control*

*Single Quantum Imaging Sequence*

*Treated*

4.23 Tesla MRI

Proton

SODIUM MAGNETIC REASONANCE IMAGING USED IN DIAGNOSING TUMORS AND ASSESSING RESPONSE TO TREATMENT

Throughout this application, various publications are referenced in parentheses. Full citations for these publications may be found listed alphabetically near the end of the specification. The disclosures of these publications in their entireties are hereby incorporated by reference into this application in order too more fully describe the state of the art as known to those skilled therein as of the date of the invention described and claimed herein.

BACKGROUND

In vitro cytotoxicity assays can provide preliminary information about the activity of an antineoplastic agent against a particular solid tumor. These techniques are limited not only by the difficulties in obtaining fresh tumor tissue for culture, but also in culturing human cells in explant. In vivo assessment of antineoplastic activity is limited by the length of time required for a change in size in a measurable soft tissue lesion to occur, which can sometimes be weeks. Moreover, some cancers metastasize predominantly in bone, and cannot be accurately measured by computer tomography (CT) or magnetic resonance imaging (MRI). Therefore, some patients have ineffective drugs administered needlessly until clear progression is observed in a CT scan or MRI, or clinical symptoms worsen. Apoptotic changes, however, can be observed in vitro within hours of exposure of a cancer cell to antineoplastic agents. An in vivo assay of chemotherapeutic efficacy in real time would significantly contribute to patient management by providing information regarding the activity of a drug thereby optimizing or discontinuing therapy in the patient.

Changes in intracellular sodium $[Na_i]$ have been described in a variety of biological systems during normal and pathophysiological events relevant to chemotherapy, including movement through the cell cycle, apoptosis, necrosis and transformation from normal to neoplastic tissue. Sodium nuclear magnetic resonance (Na-NMR) and Na-MRI were used in assessing intracellular sodium changes in vivo and to follow the effects of chemotherapy on a tumor $[Na_i]$. Flow cytometry, fluorescent indicators, and atomic absorption spectroscopy was used in parallel cell culture experiments to establish cell death or cellular dysfunction and changes in intracellular $[Na_i]$ during antineoplastic exposure in vitro. Detailed postmortem studies with immunohistofluorescence and culturing of tumor cells provided further confirmation of the link between cell ions and in vivo response to antineoplastics.

The ability to assess the efficacy of a particular therapy at an early stage has enormous potential utility. Hence, various recent studies have focused on this problem and examined the utility of monitoring, for example, changes in F-18 fluorodeoxyglucose (FDG) uptake as measured with PET imaging (94) and changes in cell metabolism as measured with P-31 MR spectroscopy (1, 44, 52, 75–78, 84). However, successful applications of MR imaging technique have yet to be realized. Recent advances made in MR pulse sequence strategy and the results of tissue culture experiments have independently led to selection of the Na+ nucleus as an important diagnostic target. Application of Na-MRI, as described here, weights images toward populations of sodium nuclei which are physiologically relevant to detecting tumors and monitoring their treatment.

Due to the biological importance of Na, its relative abundance, and its sensitivity, Na-NMR is a particularly useful tool for the study of physiological and pathophysiological processes. With special relevance to study of neoplasms, intracellular concentration of H+ (pH) and Na+ $[Na_i]$ is correlated with the proliferation rate of nonneoplastic and malignant cell populations (13). Increased $[Na_i]$ is presumably related to the role of Na+ influx in initiating movement through the cell cycle, and to Na+ linkage by transmembrane exchangers to both Ca++ and H+ (51, 54).

Measurement of Na content clinically has typically been done, using single quantum (SQ) NMR techniques (25, 74). A significant disadvantage of SQ NMR is the relatively larger abundance of extracellular (EC) versus intracellular (IC) [Na]. Attempts to discern $[Na_i]$ using only SQ NMR requires paramagnetic shift reagents (SRs) which have distinct disadvantages, including: toxicity, possible drug interaction, expense, and impermeability to the blood brain barrier. An alternative MR approach to measure IC Na content is based on the interaction of Na polyanions and their resultant effects on nuclear spin transitions; spin 3/2 nuclei (such as Na and K) have a nonvanishing quadrupole moment, allowing interaction with electrostatic field gradients (EFG) (30). In certain complex environments, like those occurring in the intracellular space of cells, but not in free solution (i.e. saline), multiple quantum (MQ) spin transitions occur which can be detected by specific pulse sequences—multiple-quantum filters (71, 72, 20, 69, 81, 95, 45). Thus, the presence of an MQ signal can be used to identify populations of Na nuclei by their molecular environment and to detect changes in $[Na_i]$ without the use of. shift reagents (18, 20, 37, 39, 91, 92, 20b).

This invention uses sodium MRI rather than the traditional proton MRI or phosphorous MRI. Sodium MRI is currently an ignored area in the field of commercial clinical imagers. Despite its promise due to the importance of sodium in so many cellular/organ systems, Na-MRI has failed to reach its full potential due to problems with discerning intracellular from extracellular populations of sodium nuclei. Shift reagents, which can be used in some experimental systems, are prohibited clinically. This invention distinguishes a responsive population of sodium nuclei, intracellular in origin, which responds to chemotherapeutic agents. Furthermore, this experiment weights these sodium MR images to enhance the contribution of the responsive population of sodium nuclei. Since this is done, using single quantum pulse sequences, it is readily applicable in current clinical imaging systems.

This invention utilized two human tumor lines as subjects and two representative drugs as antineoplastic agents (both of significant clinical importance, having different modes of action) illustrate that the disclosed technique can detect the response to the chemotherapy administered at an equivalent human dose level.

Defining intracellular concentration in a subcellular micro environment requires precise definitions of the dimensions of the physical domain of interest, its particular cellular location, the time frame over which the measurement is made, and the definition of concentration (as distinct from activity). It has long been known that determining intracellular sodium and total sodium with measurements based on ion selective micro electrodes, fluorescent dyes, atomic absorption spectroscopy, single quantum Na NMR, multiple quantum filtered Na NMR, electron probe microanalysis or flame photometry give different values. These values vary depending on to what extent the measurement is dependent on the ability of sodium to bind to the measuring probe. Thus since biological sodium is bound and unbound to different extent, or is sequestered in subcellular compartments, free activity varies and all sodium are not counted equally. Furthermore, there is different access of probes like fluorescent dyes. Finally, the relaxation times vary dependent with subcellular and molecular domains, with varying availability of insoluble binding entities, and with local diffusion properties. The biological literature is based on such qualified and often conflicting measurements, or on precisely defined measurements with vary imprecise biological significance. The level of precision required to quantify sodium in these images whose pulse sequences are herein taught must be assessed in the context of the standards of research fields whereby such control values or changes in sodium have been measured with other techniques and given predictive values or other significance (15, 16, 48).

A novel aspect of the MRI acquisition procedure described herein is the use of two different weightings (a weighted image and a non-weighted image) and the quantitative use of these two images to numerically derive two additional images which represent average estimated spatial profiles of important pathophysiological parameters of great clinical interest. As the phantoms represent known and spatially homogeneously distributed values of the two parameters, it is possible to link the two derivative images to real units and values.

This approach for functional imaging of tumors during chemotherapy using sodium MRI uses old techniques in an unexpected way. Its high level of relevance is associated with a high level of practical and immediate outcome, since the noninvasive nature of this diagnostic method would make it readily available for pilot studies with human subjects.

SUMMARY OF THE INVENTION

The deficiencies of the prior art are substantially ameliorated in accordance with the present invention, which is, in one aspect, an optimized sodium magnetic resonance imaging technique for enhancing intracellular sodium and diagnosing of tumors and their response to chemotherapy.

The present invention provides a method for acquiring magnetic resonance data from a sample comprising (a) applying a radio frequency pulse to a sample in a magnetic field, thereby causing alignment of nuclei populations within the sample; (b) applying a radio frequency pulse at a set time interval ($T_I$), thereby causing a measurable signal in the transverse plane; (c) suppressing a nuclei population in the sample by suitably selecting ($T_I$) or by applying a multiple quantum filter;(d)applying image encoding for signal acquisition of the sample in (a); (e) detecting and analyzing the output signal to obtain a weighted image; (f) applying the magnetic field to the sample in (a); (g) detecting and analyzing the output signal to obtain an unweighted image; and (h) comparing the weighted and unweighted images.

In addition, the present invention provides a method of determining the effectiveness of chemotherapy comprising
 (a) administering a dose of an antineoplastic agent to a subject prior to surgical removal of a cancerous tumor,
 (b) applying the method for acquiring magnetic resonance data from the subject; and (c) using the data obtained by applying the method for acquiring magnetic resonance data to determine if the antineoplastic agent has altered the nuclei populations in the subject.

Further, the present invention provides a method for detecting and characterizing tumors in a subject comprising (a)applying the method the method for acquiring magnetic resonance data to the subject, and (b) using the data obtained by applying the method for acquiring magnetic resonance data to determine the nuclei populations in the subject.

Finally, the present invention provides a method for determining cell death or cellular dysfunction in a subject by (a) applying the method for acquiring magnetic resonance data to the subject; (b) using the data obtained by applying the method for acquiring magnetic resonance data to determine the nuclei populations in the subject; and (c) comparing the weighted and unweighted images.

Figures 1, 1B:
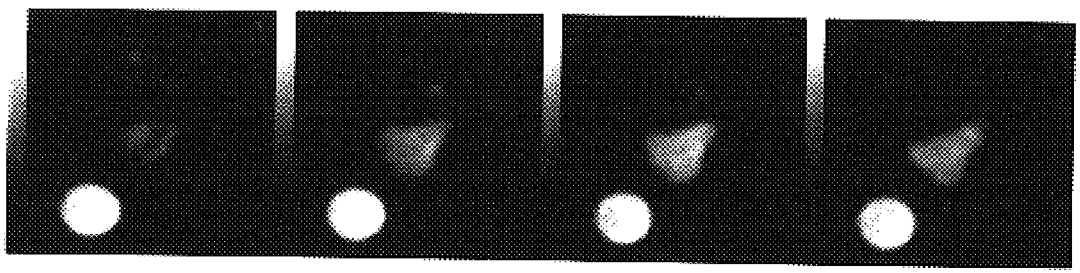
FIGS. 1A and B (A) Effects of inversion time on tumors and phantoms-All imaging experiments were performed on a high field (4.23 Tesla) whole body MRI system at the Columbia University Hatch NMR Center. A small quadrature birdcage radiofrequency coil (50 mm ID, Morris Inc.) and a high strength gradient insert coil (30 mT/m, Bruker model G-33) were employed in this study. Two phantoms (1 M NaCl, open circles; 1 M NaCl plus 4% Agarose, filled circles) were examined during single quantum acquisition and for nine different inversion recovery times ($T_I$). Single quantum was plotted as zero inversion time. Data points represent image intensity for each phantom. The lines are the theoretical relationships assuming $T_1$'s of 27.4 and 43.3 msec (based on best inversion times of 19 and 31 msec, i.e., the minimum of each curve); i.e., intensity of IR signal varies like $ABS|(1-2 \exp(-T_I/T_1))|$. Insert shows a cystic tumor, which was predominantly fluid, as verified with needle aspiration and dissection. The results of employing an optimal inversion time (right insert) versus omitting the inversion pulse (left insert) are shown. The signal from the extracellular fluid, compromising most of the tumor in the image, was completely suppressed for the best inversion time, $T_I$=25 msec, at which time, the NaCl phantom with the highest sugar (right phantom) was relatively brightest. This indicates that 25 msecs are a good inversion time for suppressing extracellular fluid, an inversion time slightly shorter than for free solution (graph, open circles). See the caption, FIG. 2 for imaging parameters. (B) Four slices from a 3D gradient echo image of a DU145 tumor are shown. The encapsulated tumor was predominantly fluid, as verified with needle aspiration and dissection. The results of changing the inversion time and omitting the inversion pulse are shown. The signal from the extracellular fluid, comprising most of the tumor in the image, was best suppressed at an inversion time of 25 msec, at which time, the NaCl phantom with the lower Ficoll concentation (left hand phantom) was also suppressed. Only in this set of images is the high Ficoll concentration phantom enhanced. All other imaging parameters are the same as in FIG. 3. This indicates that 25 msec is a good inversion time for suppressing extracellular or free sodium.

Comparison of two cell lines and two pulse sequences —A plastic animal platform was constructed to which were glued two reference phantoms of 200 mMol/L NaCl with either 30% Ficoll (P1) or 40% Ficoll (P2). The 40% phantom is the brightest phantom on the IR image and the 30% phantom the brightest on the SQ image. During the approximately 1.5 hrs of anesthesia induced by a single injection, we were able to acquire a 24 slice 3D gradient-echo single quantum image (acquisition time 15 mins) and subsequently, an inversion recovery image (45 mins). One slice each from a 3D gradient echo image of a DU145 tumor (panels A & B)

and PC3 tumors (panels C & D) show a single quantum (left panels, A & C), and inversion recovery acquisitions (right panels, B & D). Acquisition parameters were: TR=100 msec, TE=5.6 ms, FOV=40 mm, slice thickness=2.5 mm, inversion time=25 msec, and flip angle=90°. An acquisition matrix was 64×64×8. Both inversion and excitation pulses are non-selective. Tumors (indicated by straight arrows) are bright in all image sets, but are dominant in the IR images. Note that kidneys (curved arrows, panel C) are also bright in the SQ image, but completely suppressed in the inversion image (D). For better definition and confirmation of tumor structure and kidney position, paired proton and sodium quadrature birdcage coils, identical in the dimension, were used to obtain proton images (not shown) immediately after Na images, and with the animal position still maintained in the plastic animal platform.

FIG. 3

Chemotherapy, cellular apoptosis, ion activity Cells were cultured and drugs added to media for various times. Fluorescent endlabelling techniques for flow cytometry have been described in detail (23, 97). As confirmed in our lab, the APO-BRDU endlabelling technique (Phoenix Flow Systems) gives a dynamic range of fluorescence intensities of up to 1000 fold comparing control cells to cells with high levels of DNA fragmentation. TdT attaches BrdU to DNA ends, following which fluorescent antibodies for BrdU tagged the DNA fragments. Propidium iodide (PI) gives cell cycle position. One dimensional histograms compare endlabelling fluorescence for DU145 cells before and after 24 hrs exposure to VP-16; this is the most effective cell/drug combination at this early time point (panel A).

Enhanced FITC fluorescence (annexin positive response; panel B) indicated reorientation of phosphatidylserine within the cell membrane. PI was added to detect dead cells, which was both PI and annexin positive, the latter response due to internal binding of an antibody to phosphatidylserine sites accessed through membrane rupture. Control cells were mostly PI and FITC negative. The percentage of live PC3 cells that were annexin positive (vertical axis) is plotted versus time (horizontal axis) for taxotere (10 nM; filled circles) and VP-16 (10 ug/ml; filled triangles). A one dimensional annexin histogram (FITC intensity) for live cells is shown for control (bottom insert) and after 24 hrs VP-16 (top insert). Flow cytometry was performed on the Becton/Dickenson FACStar II (APO-BrdU) or exCaliber flow system (Annexing) at the Columbia University Cancer Center and analyzed using CellQuest Software.

For ion measurements (panels C & D), plates were run on a Fluoroskan II fluorescent plate reader (Titertek) using Titertek's computer Interface. Fura II loaded wells (panel D) had measured fluorescence intensities between 15,000 and 25,000 units whereby dye free wells had values ~100 and 500. The wells with SBFI/AM loaded cells (panel C) had intensities between 4,000 and 9,000 units. Two excitation values were used for each well measurement. Ratios were derived by dividing fluorescent intensity at 345 nm excitation by that at 390 nm, both with a 508 nm mission filter. For all plates, dye free wells were examined for both control and drug treated cells, and served as background values for each wavelength. For $[Ca_i]$ experiments a second means of determining background fluorescence, which gave statistically similar results, was exposure to 6 mM $MnCl_2$ following the initial measurement. This has been shown to quench Fura II, but not signals due to other $Ca^{++}$ dependent autofluorescence (73). Backgrounds were subtracted from each cell in the protocol grouping prior to the ratio being derived. These individual well to well ratios for each protocol grouping were averaqed and used in the statistical tests which determined whether the changes in $[Na_i]$ and $[Ca_i]$ following drug application were significant. Each value plotted below consisted of at least n=5 well ratios. As an additional control, we induced an acute $[Ca_i]$ response in some control wells for each plate by adding thapsigargin after the initial measurement. Rapid and large $[Ca_i]$ changes were detected in each case. To derive concentration values from the fluorescence readings, different, but standard approaches (26, 73), were taken with each dye. Both panels C and D show elevation of ion activity developing within 2–6 hours, and in the most part continuing for 18–24 hours.

Figures 1, 4A:
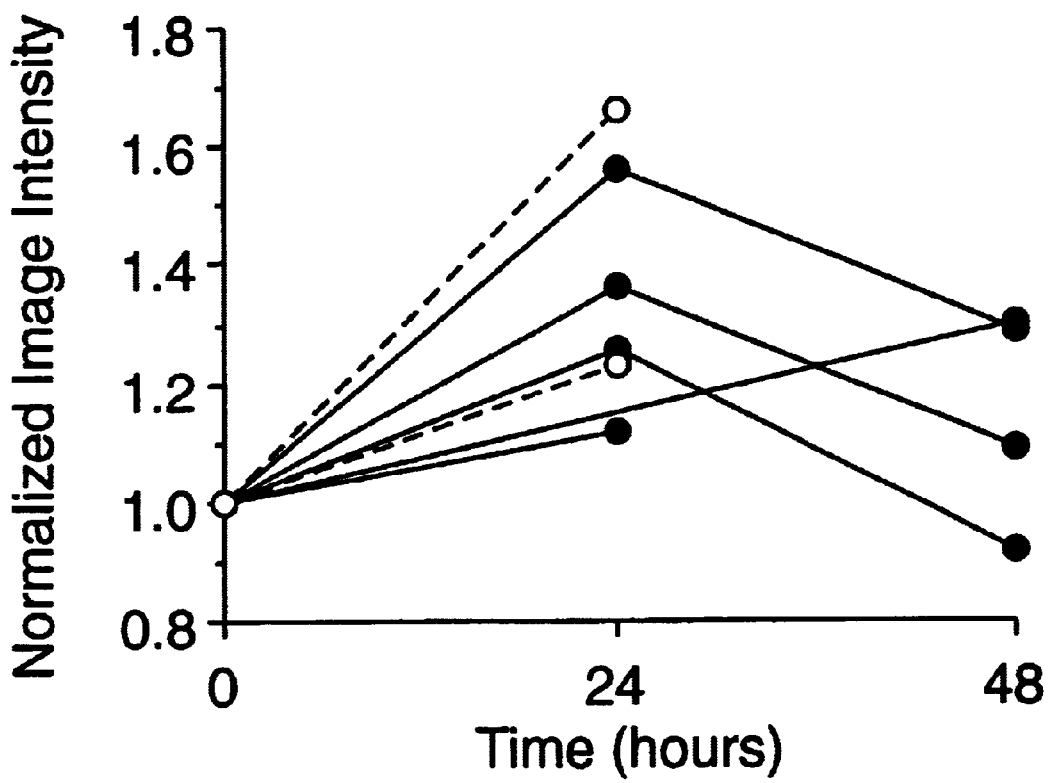
Figures 2, 4A:
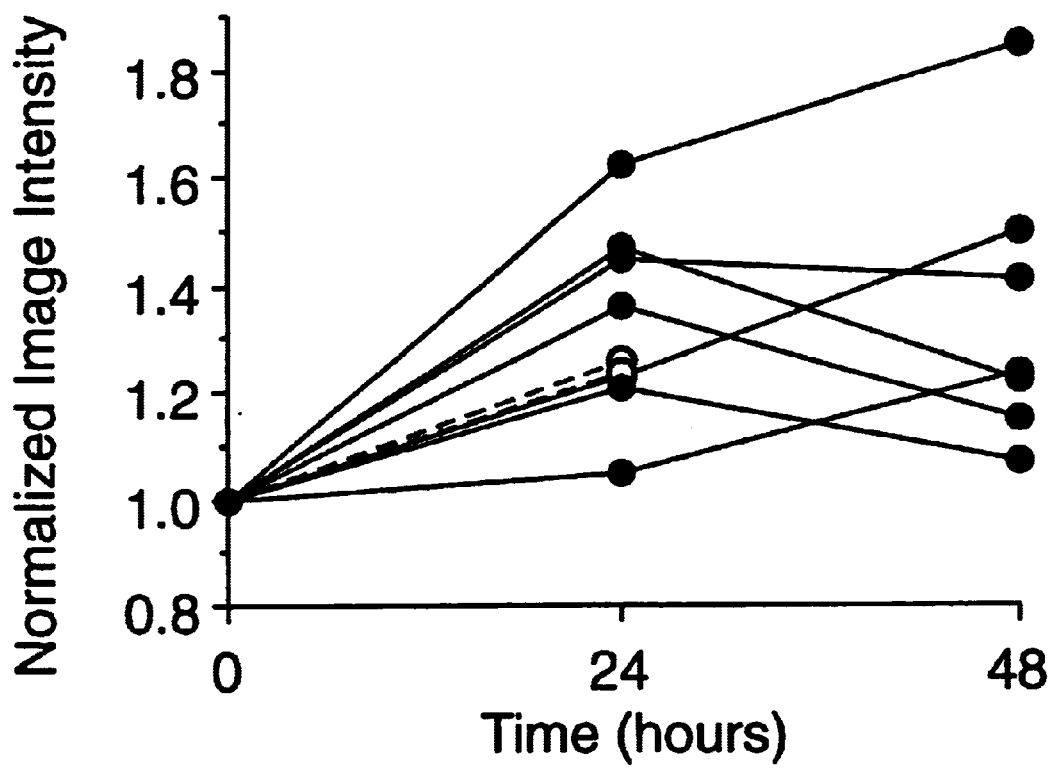

FIGS. 4A and B (A) Graphs of normalized image intentsity versus time.

(B) Graph of mitotic figure/field versus IA change. The y-axis is the mean mitotic figures and the x-axis is the IR intensity change.

Figures 1, 2, 5A:
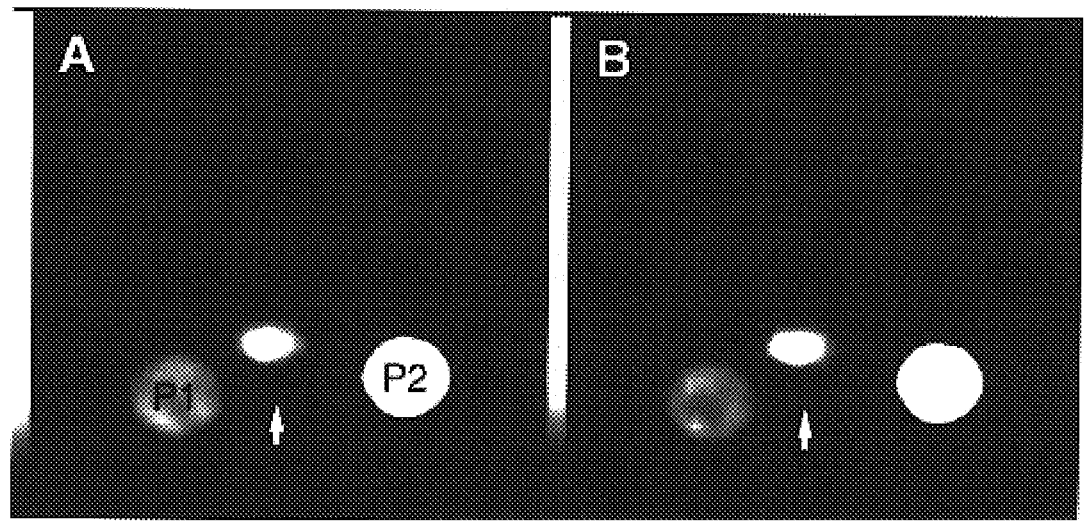

FIGS. 5A and B (A) Chemotherapy and inversion recovery MR imaging—Following acquisition of control images, antineoplastics were administered. All IR images and SQ images were normalized to the brightest phantom within each slice (i.e., 40% Ficoll for IR and 30% Ficoll for SQ respectively). All tumors were analyzed by examining changes in intensity at the brightest—usually central area—of the tumor image. It was clearly identifiable both from manual examination with line profiles or from the pixel density histogram derived from a region of interest analysis. The graphs consistently show increased image intensity at 24 hrs versus control (see text for further discussion) for both taxotere (top graph) and VP-16 etoposide (bottom graph). Results from PC3 tumors (solid lines, filled circles) and DU145 tumors (dashed lines, open circles) are plotted together. In two experiments with control saline injections (not shown in graphs), there were small decreases of 5.5% (NS) at 24 hours and 3.5% (NS) at 48 hours.

Sample pre (panels A & B) and post chemo (panels C & D) images are shown for two adjacent slices. An expansion of bright area post chemo for the IR images can be seen.

Figure 3B:
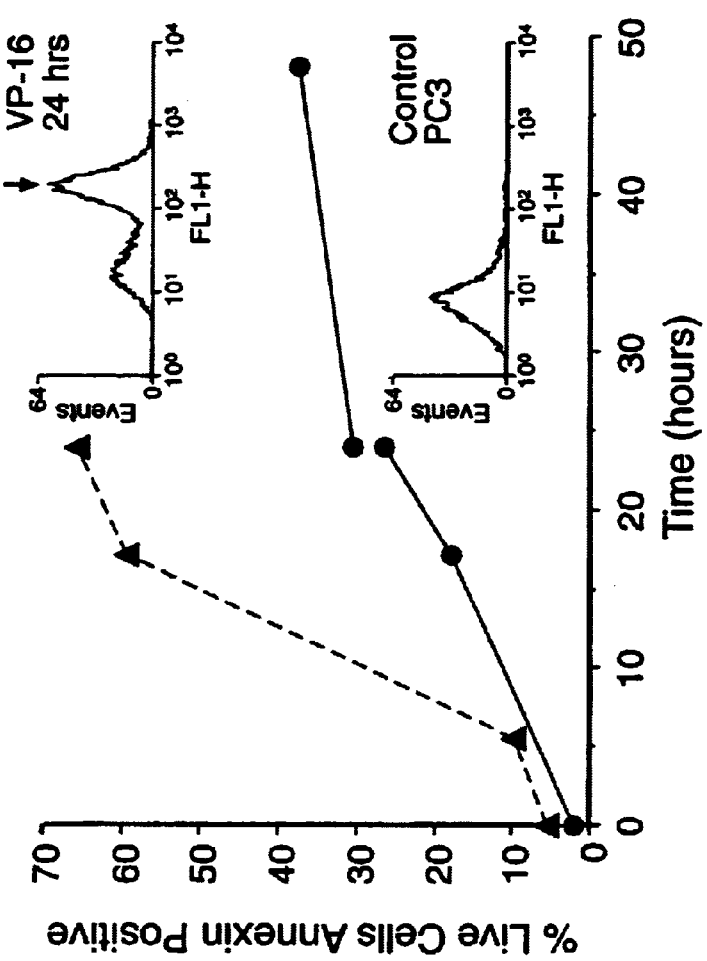
Figure 3A:
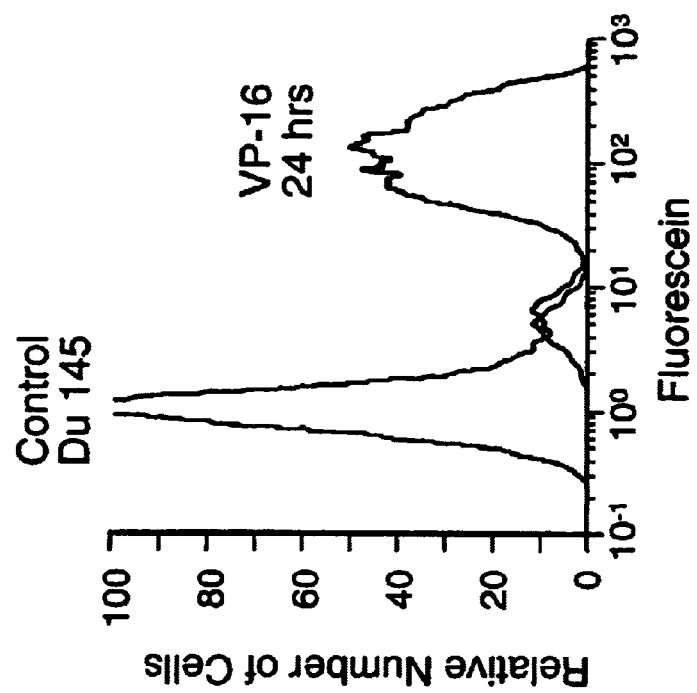

The MRI studies on individual mice post chemotherapy is limited by the limited life time of nude mice outside the sterile animal barrier. We can readily acquire control images, with 1–2 post chemotherapy re-imagings at intervals of 24 to 72 hours. In most cases mice survived several days and were sacrificed while showing no signs of behavior or health impairment. The anesthetized mouse was aligned in a deep grove with the tumor positioned through a small elliptical opening, thus maintaining the same relative position from experiment to experiment and routinely aligning the tumor just slightly above the plane defined by the two phantoms. (B) The image of an immunofluorescent slide of the tumor from FIG. 5A is shown. The DNA is fluorescently endlabelled on slides using the APO-BRDU kit (Pheonix Flow Systems) adapted from flow cytometry (FIG. 3A). The bright area on this digitized image indicates apoptotic cells occurring within the dark surviving rim, but outside of the necrotic center.

Figures 1, 6A:
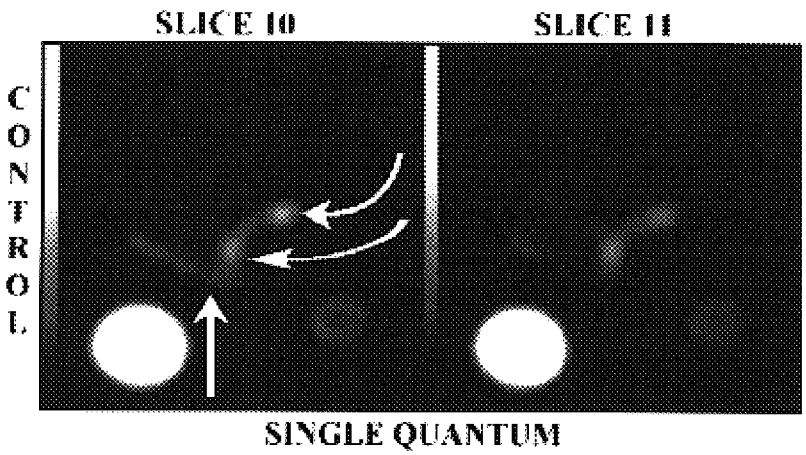
Figures 2, 6A:
Figures 3, 6A:
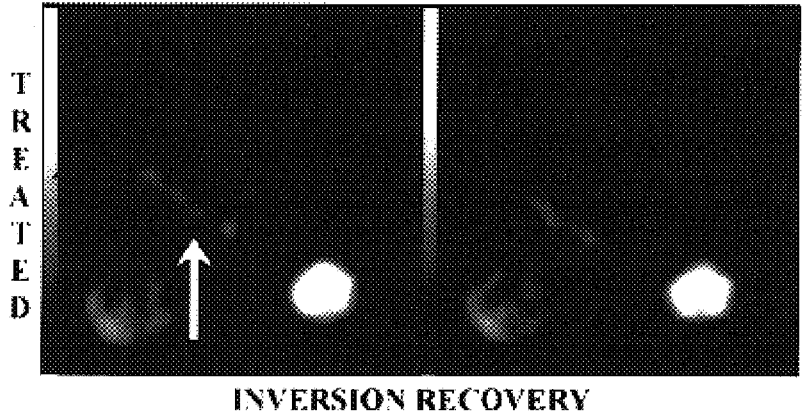

FIGS. 6A and B (A) Single quantum and inversion recovery images (before and 24 hours after chemotherapy) from a tumor bearing mouse. This noodle shaped tumor, due to its small size was only visible after chemotheray enhanced the image intensity. (B) The IR images of this tumor indicate that the necrotic center (confirmed by histology) is dark when weighted for intracellular sodium, but bright across the tumor when unweighted—measuring total sodium.

FIG. 7

This figure shows effect of 6 mg taxotere on a carcinogen (MNU) induced breast tumor in a Sprague Dawley rat. The weighted (IR) images become brighter after the treatment.

FIG. 8

A proton image of the mouse is shown along with companion IR and SQ sodium images from a tumor bearing mouse. Proton SQ sodium, and IR sodium images are shown for the same approximate slice location. The subcutaneous PC3 cell prostrate cancer tumor and kidneys are clearly visible on the proton image. The kidneys, which are bright on the SQ image with no inversion pulse, are suppressed in the IR sodium image. The tumor is enhanced in the sodium IR image. The proton image was acquired with a 2 D spin echo sequence, TE/TR was 25 ms/700 ms, slice thickness was 3 mm, NEX was 2, and acquisition matrix was 256× 256. SQ and IR Na images were acquired with 3D gradient echo based sequences with acquisition matrix 64×64×12. Both inversion and excitation pulses are non-selective. The nude mouse was positioned in a special holder to which were permanently attached two reference phantoms (left and right respectively were 30% and 40% Ficoll in 200 mM NaCl). The tumor was positioned through a small oval opening in the holder platform, which standardized its position with reference to the phantoms. This allowed for reproducibly positioning the tumor and body during different imaging sessions. The proton and sodium quadrature birdcage coils employed here are identical in dimension.

FIG. 9

Illustrates a 3D volume gradient echo technique for the weighted image.

FIG. 10

Illustrates a 3D slab gradient echo technique for the weighted image.

FIG. 11

Illustrates a 3D volume projection reconstruction technique for the weighted image.

FIG. 12

Illustrates a 2D gradient echo technique for the weighted image.

FIG. 13

Illustrates a 2D-spin echo technique for the weighted image.

FIG. 14

Illustrates a 3D-spin echo technique for the weighted image.

DETAILED DESCRIPTION OF THE INVENTION

The present invention provides a method for acquiring magnetic resonance data from a sample comprising (a) applying a radio frequency pulse to a sample in a magnetic field, thereby causing alignment of nuclei populations within the sample; (b) applying a radio frequency pulse at a set time interval $(T_I)$, thereby causing a measurable signal in the transverse plane; (c) suppressing a nuclei population in the sample by suitably selecting $(T_I)$ or by applying a multiple quantum filter; (d) applying image encoding for signal acquisition of the sample in (a); (e) detecting and analyzing the output signal to obtain a weighted image; (f) applying the magnetic field to the sample in (a); (g) detecting and analyzing the output signal to obtain an unweighted image; and (h) comparing the weighted and unweighted images.

In an embodiment the radio frequency pulse is 180° followed by 90°. In another embodiment the radio frequency pulse includes but is not limited to selective, non-selective, single or composite, sinc, sech or tyco.

In an embodiment of this invention the data acquired is two-dimensional data or three-dimensional data. In another embodiment the data acquired includes but is not limited to with slice selection or without slice selection, with or without projection reconstruction, with or without spin-echo, with or without gradient echo.

In an embodiment the magnetic field is generated by a magnet having an arbitrary field strength. In a further embodiment the magnetic field is generated by a magnet having a field strength of 1 to 5 tesla. In another embodiment the field strength is 1 to 15 tesla. In still another embodiment the method for acquiring magnetic resonance data the magnetic field is generated by a magnetic coil having a field strength of 4.23 tesla.

In an embodiment the magnetic coil is tuned for protons, sodium, nuclei of a single element or nuclei of multiple elements.

In yet another embodiment the coil is tuned for sodium. In another embodiment the coil is multiple tuned. The present embodiment includes but is not limited to multiple tuning with or without use of surface coils. In accordance with the method of this invention the magnet can be a single magnet or multiple magnets.

In accordance with the method of this invention the set time $(T_I)$ is the time which suppresses detection of a population of nuclei, wherein set time $(T_I)$ comprises the time which suppresses detection of a population of nuclei and $(T_I)$ is $(\ln 2)T_1$, $T_1$ is the longitudinal relaxation time of the suppressed nuclei. In one embodiment $(T_I)$ includes but is not limited to 25 msec. In the practice of this invention suppression comprises minimization of the signal of a population of nuclei. In an embodiment of this invention suppression includes but is not limited to the use of phantoms.

In accordance with this invention said detecting and analyzing is of intracellular and extracellular populations of nuclei. As practiced in this invention the intracellular and extracellular populations of nuclei have different longitudinal relaxation times.

In an embodiment of this invention the weighted image and the unweighted image are compared. In a further embodiment the weighted image and the unweighted image comparison includes but is not limited to pixel to pixel, region to region, or algebraic.

The present invention also provides a method of determining the effectiveness of chemotherapy comprising (a) administering a dose of antineoplastic agent to a subject prior to surgical removal of a cancerous tumor;

(b) applying the method for acquiring magnetic resonance data from the subject, and (c) using the data obtained by applying the method of claim 1 to determine if the antineoplastic agent has altered the nuclei populations in the subject.

For the purposes of this invention, the methods of administration are to include, but are not limited to, administration cutaneously, subcutaneously, intravenously, parenterally, orally, topically, or by aerosol.

Further, the present invention provides a method for detecting and characterizing tumors in a subject comprising (a) applying the method for acquiring magnetic resonance data from the subject, and (b) using the data obtained by applying the method for acquiring magnetic resonance data from the subject to determine the nuclei populations in the subject.

Finally, the present invention provides a method for determining cell death or cellular dysfunction in a subject comprising (a) applying the method for acquiring magnetic resonance data from the subject, and (b) using the data obtained by applying the method for acquiring magnetic resonance data from the subject to determine the nuclei populations in the subject.

As used herein, the term "sinc" shall mean sin x over x.

As used herein, the term "sech" shall mean the hyperbolic segment of x.

As used herein, the term "tyco" shall mean the composite pulse sequence for inversion of the signal magnetization.

The following terms are used herein and are meant to mean the following:

Doubly tuned coil—a coil which can be simultaneously tuned to two Larmer frequencies (for example, to those of protons and sodium), thus permitting MR acquisitions of both nuclei.

Gradient echo—spin echo produced by reversing the direction of a magnetic field gradient or by applying balanced pulses of magnetic field gradient before and after a refocusing (RF pulse) so as to cancel out the position-dependent phase shifts that have accumulated due to the gradient. In the latter case, the gradient echo is generally adjusted to be coincident with the RF spin echo.

Image acquisition time—time required to carry out an MR imaging procedure comprising only the data acquisition time. The total image acquisition time is equal to the product of the repetition time, TR; the number of signals averaged, NSA; and the number of different signals (encoded for position) to be acquired for use in image reconstruction. The additional image reconstruction time also is important to determine how quickly the image can be viewed. In comparing sequential plane imaging and volume imaging techniques, the equivalent image acquisition time per slice must be considered, as well as the actual image acquisition time.

Longitudinal relaxation—return of longitudinal magnetization to its equilibrium value after excitation; requires exchange of energy between nuclear spins and the lattice.

Magnetic field—the region surrounding a magnet (or current-carrying conductor). Magnetic field is a vector quantity; the direction of the field is defined as the direction that the north pole of a small magnet points when in equilibrium. A magnetic field produces a magnetizing force on a body within it.

Magnetic resonance data—signal acquisition by use of a magnetic resonance system and a specific pulse sequence.

Phantom—an artificial object of known dimensions and properties used to test aspects of an imaging machine.

Pixel—acronym for a picture element; the smallest discrete part of a digital image display.

Projection-reconstruction methods—essentially based on Fourier transformation of the free induction decay (FID) signals that are obtained by rotating a magnetic field gradient with subsequent back projection to determine the spin-density function.

Pulse, 90 degrees—Radiofrequency (RF) pulse designed to rotate the macroscopic magnetization vector 90 degrees in space as referred to the rotating frame of reference.

Pulse, 180 degrees—RF pulse designed to rotate the macroscopic magnetization vector 180 degrees in space as referred to the rotating frame of reference.

Pulse sequences—set of RF (and/or gradient) magnetic field pulses and time spacings between these pulses; used in conjunction with magnetic field gradients and NMR signal reception to produce NMR images.

Radiofrequency (RF)—wave frequency intermediate between auditory and infrared. The principal effect of RF magnetic fields on the body is power deposition in the form of heating, mainly at the surface.

Selective excitation—controlling the frequency spectrum of an irradiating RF pulse (via tailoring) while imposing a magnetic field gradient or spins, such that only a desired region has a suitable resonant frequency to be excited.

Slice—the effective physical extent of the "planar" region being imaged. The slice thus imaged is the selected slice.

Spin-echo—reappearance of an NMR signal after the FID has apparently died away, as a result of the effective reversal of the dephasing of the spins (refocusing) by techniques such as specific RF pulse sequences or pairs of magnetic field gradient pulses applied in times shorter than or on the order of $T_2$.

Suppression—one of a number of techniques designed to minimize the contribution of a particular spectral line to the detected signal. Most commonly used to suppress the strong signal from water in order to detect other components.

Surface coil—receiver coil that does not surround the body and is placed close to the surface of the body. Used to restrict the region of the body contributing to the detected signal.

$T_1$—spin-lattice or longitudinal relaxation time, the characteristic time constant for spins to tend to align themselves with the external magnetic field. Starting from zero magnetization in the z direction, the z magnetization will grow 63 percent of its final maximum value in a time $T_1$.

Tuning—process of adjusting the resonant frequency, e.g., the Larmor frequency.

Voxel—volume element; the element of three-dimensional space corresponding to a pixel, for a given slice thickness.

The practice of this invention includes the ability to assess the efficacy of a particular therapy at an early stage. Effective chemotherapy may lead to reduced F-18 fluorodeoxyglucose (FDG) uptake monitored by PET imaging (94), or, changes in cell metabolism using P-31 MR spectroscopy (44, 52, 75–78, 84). However, successful application of advanced Na-MRI techniques has yet to realized and could considerably enhance the promise of this approach.

Although the mechanistic details have not yet been elucidated (50, 60), intracellular concentration of Na+ ([$Na_i$]), but not Mg++, Pi, Cl−, or K+, are correlated with the proliferation rate of nonneoplastic and malignant cell populations (13). Further, a higher ratio of intracellular Na+/K+ is found in tumors, both benign and malignant, than in their normal cellular counterparts (57, 99). Using single quantum (SQ) NMR spectroscopy on tumors in vitro, it has been shown that [$Na_i$] varies with the state of various neoplastic tissues (56). Changes in [$Na_i$] are associated with cell cycle progression, induction of growth, and altered metastatic potential of cell lines derived from common genotypes.

Relation between [$Na_i$], and chemotherapy—Ionic alterations are important events in malignant transformation, apoptosis and necrosis. Thus it is not surprising that successful antineoplastics affect intracellular ions, and specifically [$Na_i$]. Antineoplastics can change cell cycle distribution leading to apoptosis, both of which can alter [$Na_i$] (21, 47). Antineoplastics also act on various cellular targets which may alter ion activity, including destruction of actin filaments, microtubules, or suppression of protein synthesis and metabolism. Colchicine and lonidamine, both of which induce cytoskeletal damage, increase [$Ca_i$] and alter its subcellular handling (9, 14). The topoisomerase inhibitor VP-16 etoposide elevates [$Ca_i$] and [$Na_i$] while it lowers [$pH_i$], and decreases [$K_i$] (7).

Single-quantum (SQ) and multiple-quantum filtered (MQF) Na-NMR- Due to the biological importance of Na, its relative abundance, and its sensitivity, Na-NMR is a particularly useful tool for the study of physiological and pathophysiological processes. Measurement of Na content clinically has typically been done, using SQ NMR techniques (4–6, 8, 11, 12, 25, 58, 74). A significant disadvantage of SQ NMR is due to the relatively larger abundance of extracellular (EC) versus intracellular (IC) [Na]. Attempts to discern [$Na_i$] using only SQ NMR requires paramagnetic shift reagents (SRs) which have distinct disadvantages including: toxicity, possible drug interaction, expense, and impermeability to the blood brain barrier.

An alternative NMR approach to measure IC Na content is based on the interaction of Na polyanions and their resultant effects on nuclear spin transitions (27, 30). This leads to the multiple quantum filtered (MQF) technique which is based on the multiple transverse relaxation times of Na (80). MQ Na signals have been observed in cells (31, 71, 72, 86, 90) and tissues (20, 28, 32, 33, 70, 85), as well as in studies of proteins (10, 29, 69, 71, 72, 81, 82, 90) and polysaccharides (45, 46, 90) in solutions (phantoms). Although Na nuclei will not produce an MQ signal in the type of solutions generally occurring extracellularly, interaction of the spin 3/2 nuclei with the outer surface of the cell membranes can still give rise to an extracellular MQ signal. Nevertheless, quantitation of the two populations of sodium nuclei may still be carried out solely using MQF NMR techniques without the use of shift reagents (2, 18, 20, 34, 37–43, 45, 87, 88, 92, 95).

Novel use of inversion recovery to weight Na MR Images—An unexpected technical advance capturing the utility of multiple quantum Na-MRI in a single quantum framework. The higher signal to noise of single quantum Na-MRI make it more readily implemented using current clinical systems, thus allowing for manageable acquisition times without the need of paramagnetic shift reagents. Selection of subpopulations of Na nuclei based on relaxation times uses the longitudinal relaxation time ($T_1$) rather than the transverse relaxation time ($T_2$) used by multiple quantum Na-MRI. Specifically, an inversion recovery (IR) pulse sequence is used to suppress signals from Na nuclei with long $T_1$ relaxation times. The goal was to set the inversion time at a value where Na in free extracellular solution was suppressed to produce an intracellular sodium weighted image. Total suppression of the signal from all extracellular (EC) sodium is not possible, since some may be bound to EC matrix elements and thereby relax more rapidly; nor is suppression of the signal from IC sodium nuclei with long relaxation times possible. Clearly the tumor signal is markedly reduced on the inversion image implying that the signal from a significant population of sodium nuclei has been suppressed. The resultant weighting is adequate to allow for detection of a responsive sodium pool which changes concentration following cytotoxic drug action.

Cells in culture respond to antineoplastics with apoptosis and ionic elevation—Due to the need to test applications to specific and new clinical problems non-NMR approaches were used to study cellular responses to specific drugs in the in vitro setting, whereby sodium and apoptosis can be measured together both simultaneously, or sequentially on a cell to cell or plating to plating basis. The detailed sequence of experiments presented here were used to support the imaging experimental conclusions.

Parallel tissue culture experiments were performed using PC3 and DU145 cells, and the two selected antineoplastics for the in vivo studies—taxotere (which disrupts microtubule assembly), and VP16 etoposide (a topoisomerase inhibitor). The purpose of describing these tissue culture experiments is both for (i) historical completeness in assessing confirmatory experiments using alternative techniques, and (ii) to supplement the preferred embodiment by teaching how to perform such confirmatory experimental investigations in order to employ and apply this invention to a new clinical or experimental tumor system using new drugs, new doses, and new time frames. At tissue culture concentrations approximating clinical exposures, there was apoptosis (assessed with both endlabelling and annexin V binding), and ionic elevation using fluorescent dyes for Na+ (SBFI/AM; 26, 55) and Ca++ (Fura2/AM; 35). The ionic elevation precedes the development of apoptotic markers, and has comparable dose response characteristics.

The time courses of these changes are consistent with the in vivo MRI studies described below. In addition to testing if (chemotherapy leads to [$Na_i$] elevation), the tissue culture studies provide baseline data, specifically cell cycle plots and endlabelling responses that compare treated and untreated cells in culture to cells dissociated from postmortem tumor explants.

In vivo detection of antineoplastic effects using weighted sodium MR images—Examination of the effect of chemotherapy on the IR sodium image in a series of PC3 and DU145 tumors was studied. Control and post-therapy images were acquired in sixteen mice, and tumors in two additional mice had images reacquired at both 24 and 48 hrs following control saline injection. Taken as a whole the tumors showed an increased intensity (36%+4%) following chemotherapy ($p<0.001$, $n=16$), which was also significant ($p<0.002$) versus the response to saline injections. Results are plotted as change in maximum image intensity for each drug separately (top panel, FIG. 4, taxotere; bottom panel, FIG. 4, VP-16 etoposide). Elevation is significant for each drug taken separately for the more numerous PC3 tumor experiments (taxotere, 32% increase at $p<0.001$, $n=5$; VP-16, 38% increase at $p<0.0005$, $n=7$); and is also significant for all PC3 experiments measured at 48 hrs (28%, $p<0.05$, $n=11$). DU145 tumor experiments also showed significant elevation at 24 hrs taken as a group (34%, $p<0.05$, $n=4$).

Tumors were removed from mice and examined histologically. Counts of the number of mitotic figures were significantly higher ($p<0.05$) in tumors from non-treated than from treated mice. This confirms that the tumors in treated mice were affected in another measurable way in addition to the elevation of weighted image intensity.

Cell survival and DNA fragmentation studies—As a general assay for cell survival, the microculture tetrazolium technique (MTT) (65) was used to screen a number of antineoplastics against three human PCa cell lines, namely Du145, LNCaP, and PC3. This confirmed that certain specific tested doses killed cells in the appropriate time frame. These tested doses were used in the apoptosis and ion measurement experiments. Such testing will be performed when new drugs, new clinical problems or new animal tumor models are to be imaged using the sodium MRI techniques taught herein.

This invention is illustrated in the Experimental Details section which follows. This section is set forth to aid in understanding the invention but is not intended to, and should not be construed to, limit in any way the invention as set forth in the claims which follow thereafter.

EXPERIMENTAL DETAILS

MRI

The IR pulse sequence may be used to suppress the contribution of sodium nuclei within a specific range of $T_1$, e.g. a range centered about $T_{1ex}$. Having identified this range, one sets the inversion time to $(\ln 2)$ $(T_{1ex})$, a good approximation for long repetition times. The inversion time is the time between the 180° and 90° pulses in the IR pulse sequence. In these experiments, the optimal $T_{1ex}$ is a mean longitudinal relaxation time, whereby a composite signal, predominantly extracellular in origin, which acts to mask the functionally relevant changes can be suppressed. Ability to weight for different populations of sodium nuclei was assayed using phantoms of NaCl solution, some of which contained agar or Ficoll to simulate the increased viscosity and binding sites of the intracellular space. With appropriate choices of inversion time, one could selectively and totally suppress the signal from an agar or Ficoll containing phantom, while at a different inversion time, the signal from the phantom with just NaCl was suppressed.

Two 1 M NaCl phantoms (with=open circles; and, without 4% agarose=closed circles) were examined during single quantum acquisition and for nine different inversion recovery times (see graph FIG. 1.). Data points representing image intensity while the lines are theoretical relationships (previous paragraphs) assuming T1's of 27.4 and 43.3 msec. To test the utility of this approach for weighting tumors, cells were propagated from two human prostate cancer (PC3 and DU145) subcutaneously in nude mice. Inversion times between 15 and 40 msec were examined to determine whether selective nulling of regional signal in the mouse images could be obtained as could with the phantoms. For optimum suppression of extracellular fluid, both kidneys and occasional cystic tumors were examined. (Due to the cellular origin of the tumors, a small percentage were predominantly fluid, as determined by needle aspiration and subsequent pathology). A 25 msec inversion pulse produced images with complete suppression of kidneys (compare curved arrows, panels C versus D, FIG. 2.) and cystic tumors (image inserts, FIG. 1). The inversion time producing the best suppression of fluid objects also produced the best relative enhancement of the tumor (FIG. 2.; panel B, DU145 tumor; panel D, PC3 tumor). The relative enhancement of the tumors was readily apparent on 3–4 contiguous slices from each 3D image of 24 slices.

Figures 1, 6B:
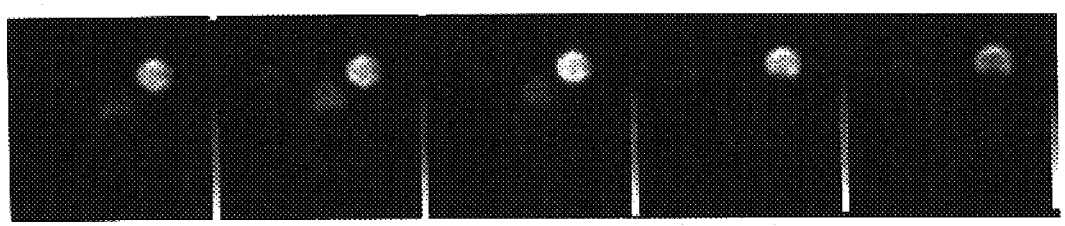
Figures 2, 6B:
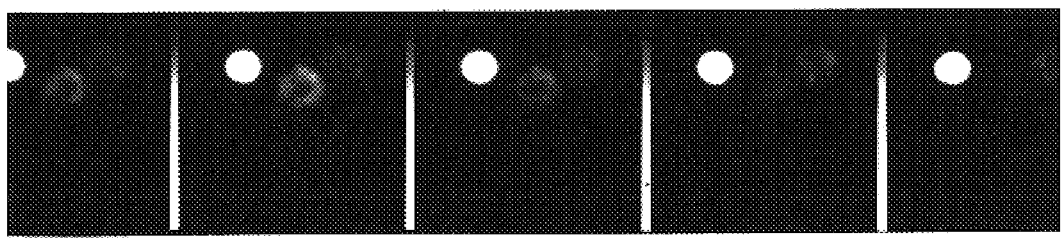
Figures 3, 6B:
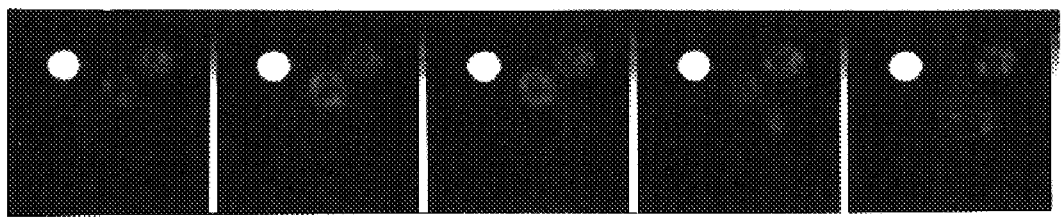
Figure 7A:
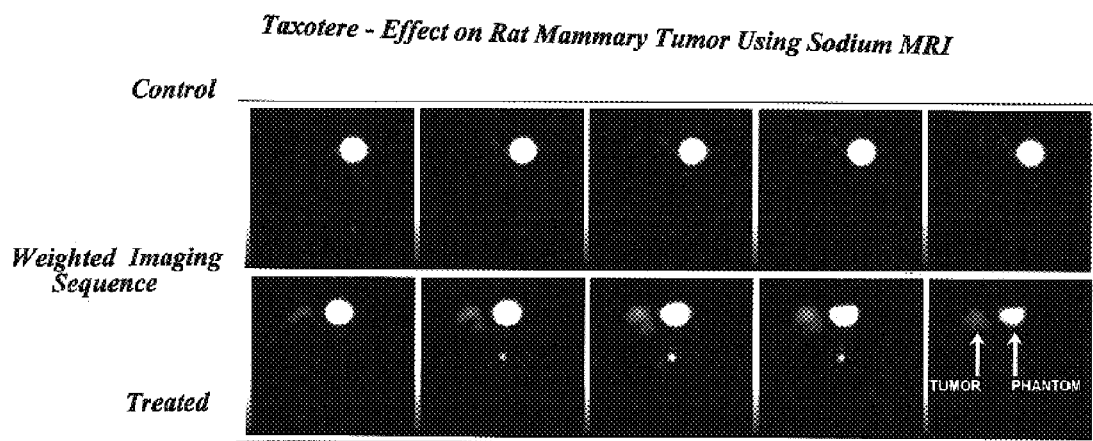
Figure 7B:
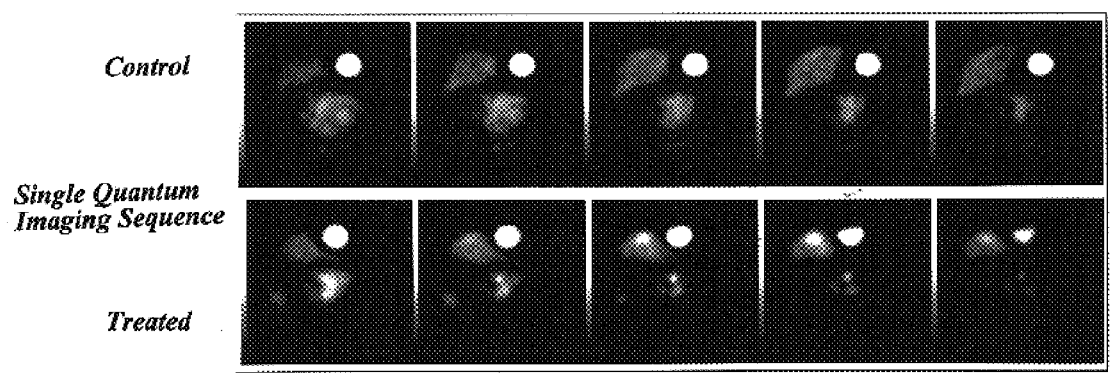

Additional experimental examples are shown in the following images. In one example, the increased intensity on the image is shown in the surviving rim of the tumor. Since most tumors greater than about 4–7 mm in diameter had outgrown their blood supply, there was usually some central necrosis surrounded by a surviving rim of live cells. This is also found clinically. (FIG. 6b).

In another example, a breast cancer tumor is imaged in an animal model. This image verifies that the imaging diagnostic described herein responds to the treatment of a different animal model when using a different tissue type as the neoplastic target. The tumor was induced by injecting a Sprague Dawley rat with carcinogen MNU. When the tumor was palpable and measured in excess of 5 mm in diameter, the rat was imaged using weighting and non-weighting pulse sequences. One rat was given a 3 mg intra venous injection of taxotere and a second was given a 6 mg injection of taxotere. Only the latter showed a response, illustrated in the FIG. (7). Both the images became brighter, with the most dramatic proportional change occurring in the weighted image.

All imaging experiments were performed on a high field (4.23 Tesla) whole body MRI system. A small quadrature birdcage radiofrequency coil (50 mm ID, Morris Inc.) and a high strength gradient insert coil (30 mT/m, Bruker model G-33) were employed. Acquisition parameters were TR=100 msec, TE=5.6 msec, FOV=40 mm, slice thickness=2.5 mm, flip angle=90°, inversion time=25 msec, acquisition matrix was 64×64×8. The two phantoms on all animal images shown were identical (P1-30% Ficoll in 200 mM NaCl; P2-40% Ficoll in 200 mM NaCl). All animal images were normalized to the brighter phantom (e.g. P1 on the SQ, P2 on the IR). Animals were positioned in a specially designed animal holder, allowing for reproducible tumor placement.

Cells were obtained from American Type Culture Collection (Rockville, Md.) grown in RPMI 1640 media (Sigma) supplemented with 5% Fetal Bovine Serum (Sigma) except LNCaP which requires 10% FBS plus ITS+(TM) (Collaborative Research, Bedford, Mass.). Cultures are initiated in culture plates, allowed to attach overnight, and treated with drugs for indicated times.

For better definition of the tumor structure, paired proton and sodium quadrature birdcage magnetic coils, identical in dimension, were tuned to obtain proton images immediately after the two Na images (with the animal position still maintained in the plastic animal platform). A set of Proton, SQ sodium, and IR sodium image are shown for the same approximate slice location. (FIG. 8) The subcutaneous PC3 cell prostate cancer tumor and the kidneys are clearly visible on the proton image. The kidneys, which are bright on the SQ image with no inversion pulse, are suppressed in the IR sodium image. The tumor is enhanced in the sodium IR image. The proton image was acquired with a 2D spin echo sequence (two-dimensional data), TE/TR was 25 ms/700 ms, slice thickness was 3 mm, NEX was 2, and acquisition matrix was 256×256. SQ and IR Na images were acquired with 3D gradient echo base sequences (three-dimensional data) with acquisition matrix 64×64×12.

Flow Cytometry

Figures 1, 1B, 2:
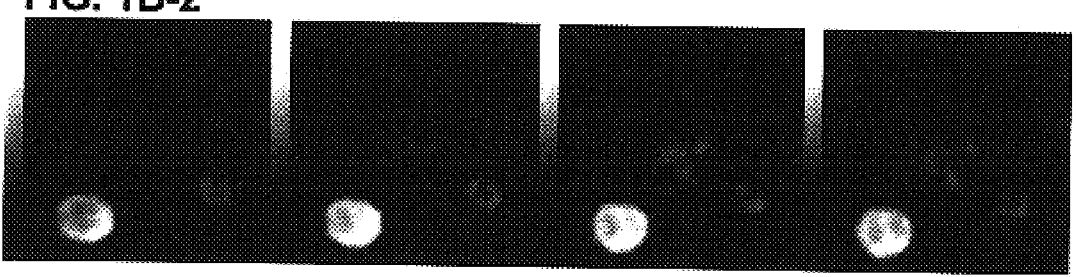
FIG. 2
Figures 1, 1B, 2, 3:
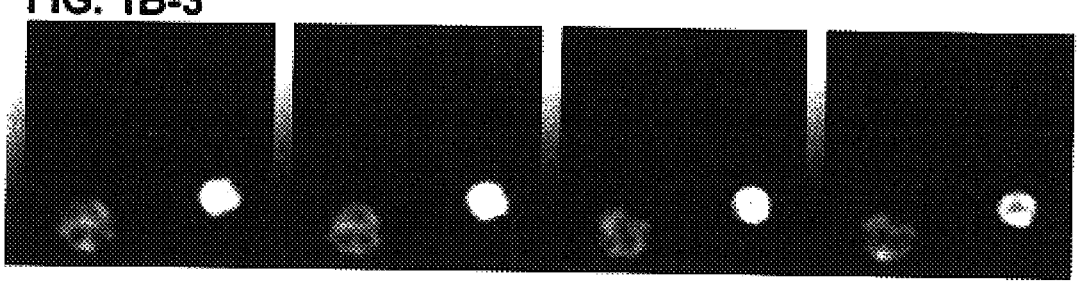

Representative data from flow cytometry (A & B) and fluorescent measurements in adherent cells C & D) are shown in FIG. 3: (A) A response at 24 hrs showing on a histogram of endlabelling intensity for the most responsive cell/drug combination (Du145/VP-16). Graph indicates a robust (100 fold) increase. No response was seen at 8 hrs, and other drug/cell combinations did not peak until 48 hrs; (B) Time course of annexin V fluorescent labeling of propidium iodide excluding cells for VP-16 (10 ug/ml; triangles) and taxotere (10 nM; circles) is plotted. Two histograms (inserts) illustrate the minimum and maximum response (second peak shows annexin V positive, PI negative cells); (C) $[Na_i]$ changes from PC3 cells in 96 well plates measured with fluorescent dyes indicating elevations of 10–20 mM (from in situ calibration technique) which start as early as 2–6 hrs (26,55); (D) $[Ca_i]$ changes as percent of control (set to 100) also shows early and persistent ionic elevation; using standard experimental techniques with Ca++ ionophores and buffers (73), absolute mean control was estimated at 126 micromolar, with average elevations of 150 micromolar. (Each data point in (C) and (D) represents mean+standard error of five cell wells.)

More mechanistic assays of survival will then be used to identify steps in the apoptotic pathway. Following chemotherapy, fixed cells have DNA strandbreaks and total DNA (propidium iodide) fluorescence labeled. This late event in apoptosis (DNA fragmentation) can then be quantitated. However, DNA fragmentation is not a requirement of apoptosis; since apoptosis can proceed in the presence of endonuclease inhibitors, which block DNA fragmentation. Therefore, a second earlier event in the apoptotic cascade will also be examined. Live cells will be exposed to an Annexin V/FITC conjugated antibody and then examined with flow cytometry. Enhanced fluorescence indicates reorientation of phosphatidylserine within the cell membrane and identifies a very early cellular commitment to the apoptotic cascade (61, 93).

At the end of the treatment period, cells are trypsinized, resuspended in media, resuspended in PBS, resuspended in iced cold methanol free formaldehyde (1% in PBS) for 15 min, resuspended in 70% ethanol and stored at −20° C. until all samples from a given experiment are ready to run (19, 23). Using a very powerful endlabelling technique (APO-BRDU, Phoenix Flow Systems, California) which gives a dynamic range of fluorescence intensities of up to 1000 fold comparing control cells to cells with advanced DNA fragmentation. Results have been confirmed using positive and negative controls provided by Phoenix Flow Systems, camptothecin treated PC3 cells, and a SNAP treated myocyte line.

Fixed cells are labeled following kit instructions (two washes with kit buffer, overnight endlabelling, two resuspensions in a rinse buffer, exposure to fluorescent antibody and treatment with propidium iodide and RNAase. Flow cytometry is performed on a Becton/Dickenson FACStar II. Individual fluorescence intensity values for 10,000 cells are obtained for each sample.

Chemotherapy Administered

Figures 3, 4, 5A:
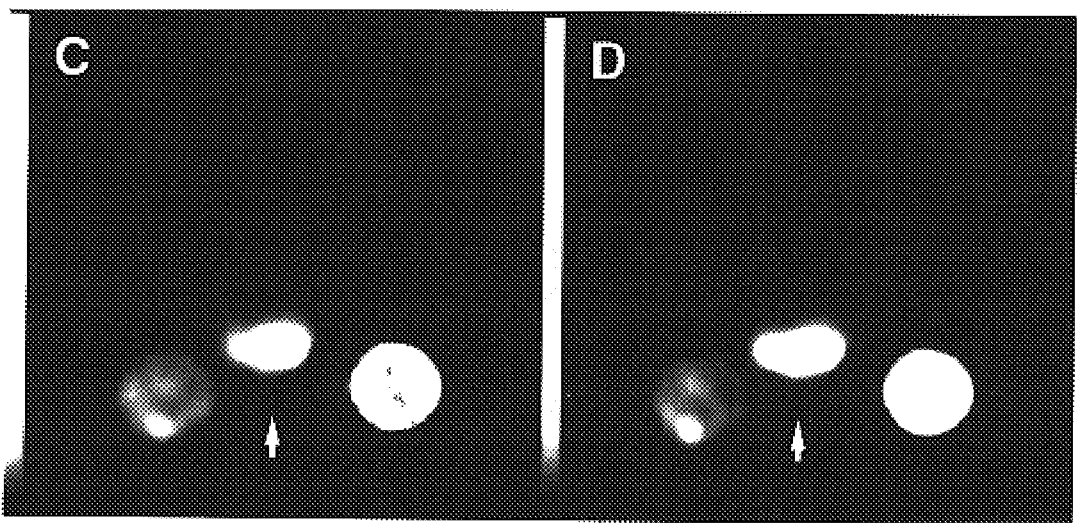
Figure 5B:
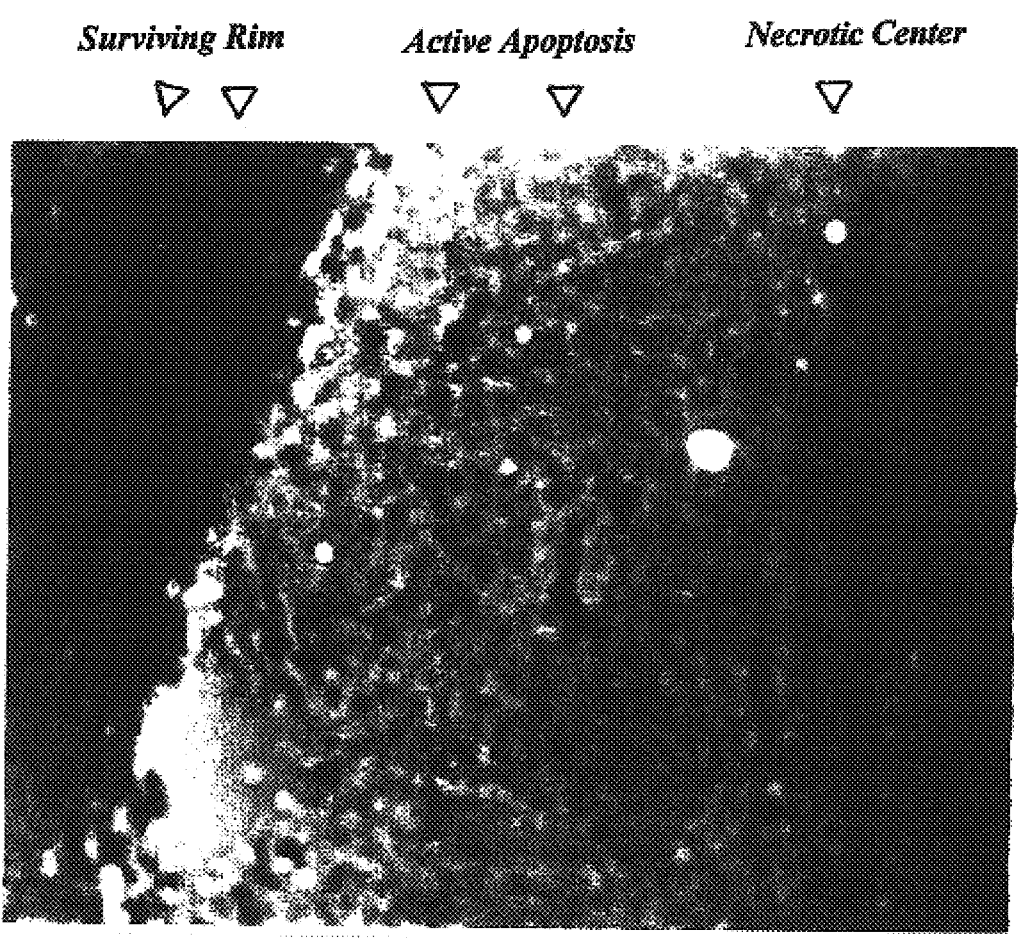

Two adjacent slices from a 3 dimensional gradient echo image set of a PC3 tumor are shown before (FIGS. 5, A&B) and 48 hrs after (FIGS. 5, C&D) injection of 1.5 mg taxotere to the nude mouse. In addition to the intensity changes, there was a clear spatial broadening of the tumor on the inversion recovery image. FIG. 5b shows with immunohistofluorescence how an area of bright apotic staining exists beneath the surviving rim. The second example illustrates the contribution of this technique at its limit of resolution. Each pair of panels (FIG. 6) shows the same pair of contiguous slices from a PC3 image set before (top two panels—single quantum; (middle two panels, inversion recovery) and 24 hr after (bottom two panels, inversion recovery) injection of 0.3 mg VP-16 etoposide. The unusual shape of this elongated tumor (4–5 mm diameter; 18 mm length) was confirmed with H&E histology and gross dissection. The tumor is nearly undetectable on the control IR image, yet is readily apparent following chemotherapy. It is seen on the SQ image along with the kidneys, which again are totally suppressed in the IR image (FIG. 6a).

Figure 4B:
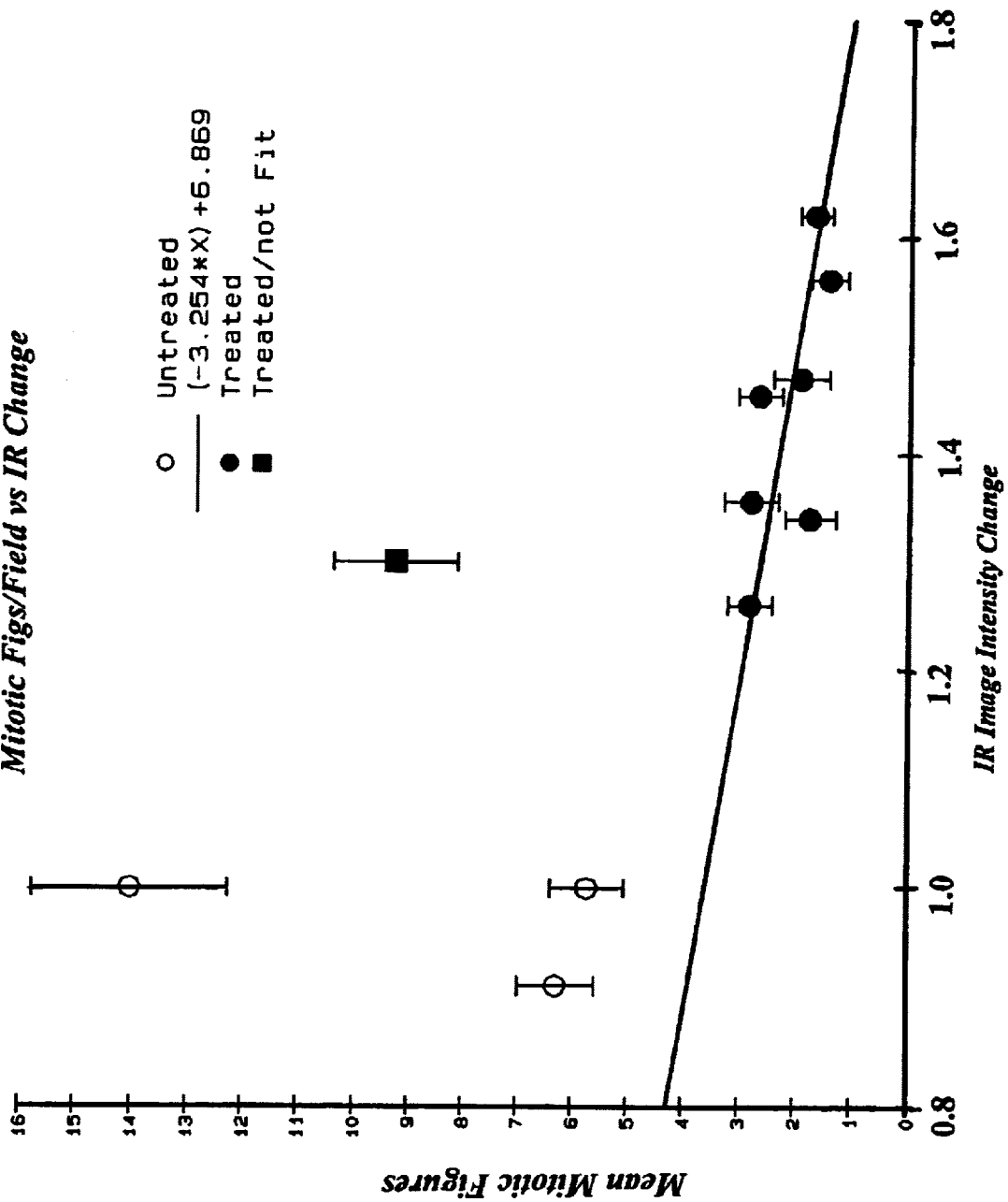

Inversion recovery images (25 msec inversion time) were acquired for 16 nude mouse tumors following chemotherapy. Mice were positioned in a plastic holder with phantoms permanently attached just below the plane of the tumor, which protruded through a small whole in the platform. The slice with the brightest tumor region was used for analysis and normalized to the brighter phantom. Peak of the line profile is plotted through the center of the tumor, and for predrug (0 hrs) and two later times (24, 48 hrs). Taken separately, the change for each drug on PC3 cells was significant—taxotere induced a 32% increase ($p<0.001$; FIG. 4A) and VP-16 induced a 38% change ($p<0.0005$; FIG. 4B). The drug responses were not significantly different from each other ($p>0.15$). Even though the signal could either continue to increase or decay toward baseline, there was still on average increased signal at 48 hours compared to control (28% n=11), with a slight decrease (NS, $p>0.196$) from the 24-hour level for the PC3 cell tumors. In two experiments with control saline injections, there were small decreases of 5.5% (NS) at 24 hours and 3.5% (NS) at 48 hours.

Four additional experiments on DU145 cell tumors (two each with taxotere and VP-16) and obtained an average increase of 34% (24 hours, $p<0.05$).

Using H&E staining of parafilm embedded and fixed (10% formalin) sections, histological studies were performed on 12 of the 16 tumors from treated mice, on the two control/saline injected mice, which were imaged over the normal time period (48 hours), and on two additional mice which received no injections and were only imaged once. Based on direct counting of high power fields, there was a significant reduction in mitotic figures ($p<0.05$) for the treated tumors indicating drug action. All tumors had some central necrosis, with a surviving rim. The largest surviving rims were in the untreated tumors. The largest contiguous area of apoptotic cells was in a treated tumor which showea a dramatic broadening of the zone of high intensity on the weighted image between 24 and 48 hours. (FIG. 5a) We interpret this to mean that the intensity change indicated a wave of apoptosis expanding radially from the necrotic center. This tumor histologically had a small necrotic center, a large apoptotic band, and a small surviving rim. The interpretation is consistent with the fact that apoptotic nuclei are not stable since small (<200 bp) DNA fragments wash out of the cells or apoptotic cells are phagocytized. (FIG. 5b).

Cell Survival and DNA Fragmentation

To specifically assay DNA fragmentation, a downstream response to apoptosis, uses of a terminal deoxynucleotidyl transferase labeling approach whereby fluorescent moieties are enzymatically attached to all DNA fragment ends. (FIG. 3a) The technique which was used, has a dynamic range of approximately ×1000 (FIG. 2). This allows for making very quantitative comparisons of DNA fragmentation on a cell to cell basis using flow cytometry, and to further examine the relative drug sensitivity profiles of the 3 cell lines. For example using taxotere and VP-16 etoposide, it was found that PC3 cell DNA fragmentation continues to develop beyond the 24-hr sample point where DU 145 response peaks and subsides. LNCaP is the slowest responding of the 3 lines with almost no response at 24 hrs, but significant DNA fragmentation at 44 hrs.

To define the magnitude and time course of survival as a function of dose we use three relevant antineoplastics, time points, and dose ranges to illustrate how one could perform the supporting experimentation using the non MRI components in order to apply this invention to a new clinical oncology problem or a study using a new animal model. The sample times start at 4 hrs and end at 3 days following administration of antineoplastics (e.g. taxotere (1 to 100 nM), 9-amino-camptothecln (10–200 nM), and VP-16 etoposide (1–100 ug/ml). The cells to be used in such drug studies could either commercially available cell lines from ATCC, or cells dissociated from tumors (treated or untreated). These three types of cells could be compared to illustrate the effects of potential in vivo mutations or genetic amplifications on cell response (ionic, apoptotic, necrosis) to drugs or the effects of drug resistance or selection on remaining cells in an in situ tumor and the subsequent response of these cells to drugs.

At the end of the treatment period, cells are centrifuged for 3 min at 1000 rpm and supernatant replaced with PBS. Fifty $\mu$L of 12 $\mu$M MTT reagent [3-(4,5-dimethylthiazol-2-yl)-2,5-diphenyl-tetrazolium bromide in PBS] is added to each well of 96 well plate. The plates are reincubated at 37° C. for 4 hr in dark and supernatant aspirated. Formazan crystals are solubilized in 150 μL DMSO at 37° C. for 30 min with gentle agitation. The absorbency per well is measure at 540 nM using an EL311 Microplate Reader (Biotek, Instruments, Inc. Winoski, Vt.). Each assay is performed in triplicate using 3–6 wells per condition at each trial.

Fluorescent Measurements of Free [$Na_i$]

We developed two different approaches to fluorescent measurement of cellular free [$Na_i$]. Each approach has its advantages. SBFI/AM is ratiometric (26, 35, 55) and is unaffected by variations in loading. However, its double wavelength ultraviolet excitation requirement is impractical for flow cytometry. Sodium green (3) uses standard Fluorescein excitation/emission wavelengths. Forward scattering is used to normalize for loading, or alternatively various Na+ insensitive fluorescent dyes (with different spectral properties but using similar loading mechanisms) are used. Using sodium green, propidium iodide (PI), and forward scattering several populations in treated DU145 and PC3 cells were identified, one of which may be an apoptotic population with elevated [$Na_i$].

Figures 1, 1B, 2, 3, 4:
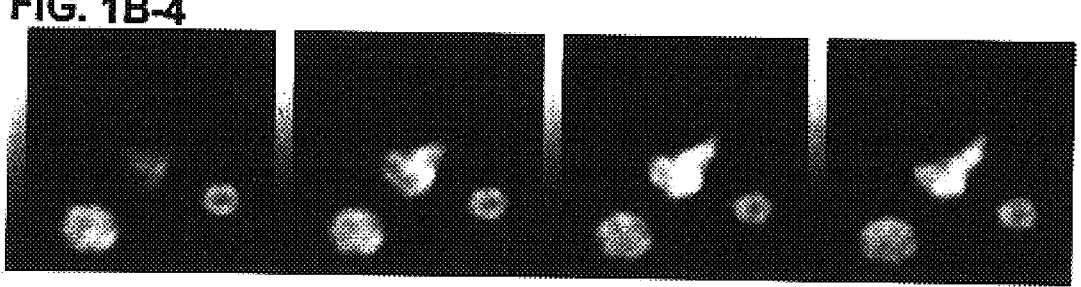
Figures 2A, 2B, 2C, 2D:
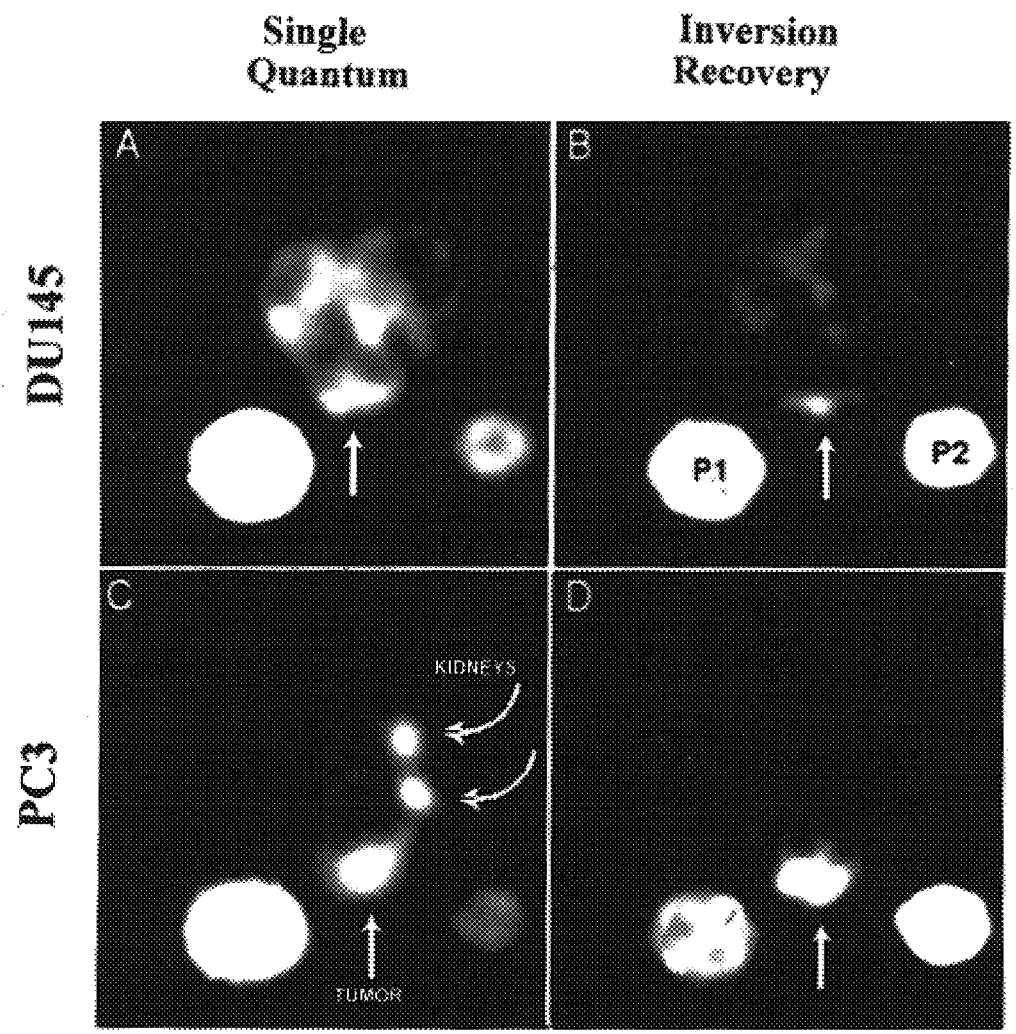

Specifically, two populations remain after gating out the high PI cells (presumably necrotic), yet have distinctly different PI intensity levels (i.e., there are 3 populations on a PI plot). These different cell populations can be characterized by: i) using Na ionophores (while varying [$Na_o$]); ii) examining the loading characteristics of Na+ insensitive dyes with similar loading mechanisms; and, iii) physically sorting the populations followed by measurements with the ratiometric Na+ sensing dye SBFI/AM. These tissue culture ionic meaurements can be made on commercially available, well studied cell culture lines. They can also be run to compare these results to those on primary cultures of cells from human tumors. Thus, cell culture response profiles for individual patients can be developed and used co better plan the imaging studies, in particular the timing of images acquisitions, and dosing and choice of the antineoplastics. Thus changes in intracellular free Na: ([$Na_i$]) was determined at various times following addition of antineoplastics to the culture media, in a similar fashion to the endlabelling flow cytometry experiments (FIGS. 3 & 4). Patterns of [Na] change can be examined in relation to an event in the apoptotic cascade, and for example, to drug and dose levels, or cell line.

Two dyes (both from Molecular Probes) were used for this purpose, SBFI/AM (26,55) and sodium green (3). Sodium green is designed for flow cytometry, and SBFI/AM, a dual excitation w avelength dye, is used in a fluorescent plate scanner. Thus with SBFI/AM, cells can be treated and cultured and adherent in black (non fluorescent) 96 well plates and measure average [$Na_i$] of the cells in each well. With sodium green, cell suspensions can be run through the fluorescence activated cell sorter, populations selected for subsequent fixation and further study, or, with proper controls and use of Na ionophores, measure [$Na_i$]. By combining the two approaches it is possible to compare average [$Na_i$] in treated versus untreated cells.

In vivo MRI Studies on Tumors Probagated From Transgenic Mouse Myocytes

A murine myocyte line (AT-1) in non athymic mice was propagated, since these mice could be subject to multiple imaging sessions. SQ and TQ images of a large AT1 tumor were acquired and noted was the higher signal intensity in tumor compared to normal tissue in the Na images. However, there is a higher contrast between tumor and normal tissue in the TQ image compared to the SQ image due to the higher sensitivity of TQ NMR to [$Na_i$].

After preliminary studies, experiments were performed where proton, Na SQ and Na TQ images and line profiles were acquired at baseline and following bolus i.v. injection of chemotherapy. Imaging results for a LNCaP tumor in vivo, both at baseline and 18 hours after i.v. injection of 1 mg of taxotere in the femoral vein were examined. While the SQ line profile did not significantly vary, there was a substantial increase in the TQ line profiles Lollowing chemotherapy, as we have also shown by NMR spectroscopy. These results indicate that change in [$Na_i$] due to chemotherapy are detectable by TQ imaging, but not SQ imaging, and illustrate the potential of using the advanced MRI techniques to follow chemotherapeutic efficacy in vivo.

Tumor propagated from the AT-1 myocyte cell line was used for an additional MR confirmation of the approach. A single tumor was removed and finely minced, then split in half and resuspended in two 50 ml Falcon tubes filled with oxygenated media. Triple quantum filtered sodium MR spectroscopy was utilized with a Bruker 400. After control spectra were acquired, the tissue was resuspended in fresh media. To one tube was added lonidamine and doxorubicin (adriamycin). This combination was recommended as synergistic. At six hours, the two tubes were again examined and the treated tumor gave a clearly higher signal, indicating sodium elevation.

The total cell content of Na can be determined with atomic absorption spectrosccpy (AAS) for cell pellets (>300 mg; 89) trypsinized from culture dishes. This is a useful measurement since Na-NMR can measure changes in total $Na_i$ in the absence of a change in [$Na_i$]. Examination of untreated cells in a pellet with AAS and revealed higher total [$Na_i$] in LNCaP than in PC3 and DU145 cell lines. This is intriguing since LNCaP also has the highest level of ambient endlabelling fluorescence. These studies will be pursued and used in combination with AAS measurements on tumors removed after imaging.

Analysis of flow cytometry was performed using standard one and two dimensional histograms and scatter plots. These studies help establish a detailed context for planning and interpreting the MRI studies described below, and may in addition elucidate mechanistic relations between [$Na_i$], apoptosis, and necrosis. Furthermore, potential users may want to perform tissue culture experiments to assist in interpreting MRI results for different cell types, clinical oncology presentations, or new drugs.

Employing the dose dependence and time course data from the tissue culture studies to plan and interpret the in vivo Na-MRI studies which use the same cell lines and antineoplastics. Following Na-MRI image acquisition, tumors are removed and postmortem cell culture and biochemical studies are performed to assess antineoplastic impact and ionic alterations.

Histopathology studies were performed to characterize the drug effects and the cellular characteristics of the postimaging tumor. Tissue was fixed in 10% formalin, parafin embedded and stained with Hematoxylin and Eosin (H&E). Tumors had a central necrosis (coagulation or liquefaction type) with a surviving rim. Between the surviving rim and central necrosis was a Legion of apoptotic cells. Proliferation was assessed by counting the number of mitotic figures per high power field. The treated tumors showed a significant decrease in proliferation as so assayed. This suggests strongly that the drugs were effective and reached the tumor cells. Furthermore, treated tumors with larger IR image increases post-chemo showed fewer mitotic figures in a field than tumors with lessor responses. (FIG. 4b).

Control images are acquired for each mouse to be treated. Both SQ and IR images are acquired. Proton MR images are acquired to define the underlying tumor structure. Potential $[Na_i]$ gradients associated with inhomogeneous distributions of necrotic tissue, rapidly growing cells (different cell cycle distribution), and non-neoplastic tissues can be examined. High resolution line profiles are obtained at different regions of the tumor. Line profiles are more rapidly acquired than full images and can be used to monitor real time changes. However, even using line profiles, with their reduced acquisition times, the triple quantum data described above was still noisy. Acquisition times are constrained to about 1–2 hours for rodent experiments, the time durino which anesthetic remains active. For clinical studies, acquisition times would be constrained by considerations of patient comfort and ability to remain motionless, and utilization/cost criteria. Thus the inversion pulse technique described with its enhanced signal to noise ration, is a significant improvement over the triple quantum filtering technique.

Post mortem tumor assays following chemotherapy and imaging: Prior to recovery from the final imaging session, mice were sacrificed, tumors recovered, fixed in 10% formalin and sectioned. Some sections can be: i) flash frozen for later histology and immunohistochemistry as required; ii) washed in PBS, treated with collageriase, suspended in serum containing medium, cultured or fixed for later flow cytometry study; or, iii) blotted and placed in liquid nitrogen for later AAS analysis. For AAS studies, 20 minutes prior to sacrifice, a 100 μL injection of 80 mM potassium cobaltic EDTA in saline is injected in a femoral artery (83, 96). Adequacy of in vivo drug levels can also be assessed by comparing flow cytometric data of cells fixed from treated tumors versus those cultured directly from commercial stocks. Parameters like cell cycle distribution and endlabelled DNA strand breaks (both from fluorescent stained DNA) are sufficiently stable during the approximately 2 hrs required to disperse and fix the cells.

Image intensity is examined as a function of propagating cell line and tumor size, and compared to normal tissue. High resolution line profiles are examined for relative changes following chemotherapy. Such changes indicate a rapid and measurable response to chemotherapy. For clinical studies, needle biopsies can be performed to histologically assess the effects of drugs on cell morphological and immunological status. If tumor removal is undertaken at this time, complete studies of morphology, proliferation index (Mibl/Ki67, Pharmingen Inc.), and apoptosis can then be performed. One goal in performing imaging studies on tumors prior to removal is to examine the drug sensitivity profile of the tumor cells in order to more effectively perform profylactic treatment of potential metastasis.

Examination of the dose and time dependence of representative antineoplastics on the survival of two established human prostate cancer cell lines in culture is examined using flow cytometry (FIG. 3). These estimates of the time course of specific, measurable markers during apoptotic cell death are important in interpreting in vivo imaging studies, in planning cell culture experiments where $[Na_i]$ is correlated with these same markers, and in postmortem flow cytometry of dissociated tumor cells. As envisioned, these cell studies can be performed for each new clinical presentation or experimental animal model to assist in planning and interpreting the imaging.

a) Early events—reorientation of phosphatidylserine: Live cells exposed to an Annexin V/FITC conjugated antibody. Enhanced fluorescence indicates reorientation of phosphatidylserine within the cell membrane (61, 93). Propidium iodide (PI) concurrently indicates cell viability. Since trypsin cleaves the annexin binding site, for dissociating cells from explanted tumor, trypsin containing collagenase preparations were not used. Cells are dissociated by mincing the tumor with surgical scissors and passing tissue repeatedly through needles while increasing the gauge. Cells are removed from tissue culture plates using 1 mM EDTA in Ca/Mg free PBS.

b) Late events—DNA strandbreaks: Fixed cells (treated and control) have DNA strandbreaks (Phoenix Flow Systems, APO-Brdu KIT) and total DNA (propidium iodide) fluorescent labeled. DNA fragmentation is quantitated by flow cytometry.

c) Treatment protocols—
Drugs and doses—Taxotere—1, 10, 20, 50, 100 nM; VP16 Etoposide—0.1, 0.3, 1.0, 3.0, 10.0, 30.0 μg/ml
Cell Lines prostate—cancer—PC3, Du145, LNCaP breast cancer—MCF7, T47D
Exposure Times—4, 8, 12, 16, 20, 24, 36, 48, 72 hours Combination therapies with multiple imaging modalities-listings of NIH sponsored clinical cancer trials indicate the potential efficacy of combining traditional chemotherapy with anti-angiogenesis therapy. Since proton MRI can be used to assess blood vessel capacity, by employing well known techniques with contrast agents; the invention taught here could readily be employed with a doubly tuned or multiply tuned coil to generate co-registered proton images with weighted and unweighted sodium images. Thus, information on chemotherapy effectiveness could be attained concurrently with that on vessel capacity in "real time". This would assist in developing new clinical protocols and testing combination drug therapies.

d. Analysis—FACS data is analyzed using software (CellQuest; Winmidi). Two dimensional histograms are used to examine endlabelling fluorescence versus PI, or annexin versus PI. In the former case, PI gives cell cycle information. In the latter, it allows for gating of dead cells.

Sodium Ion Measurement

Changes in intracellular free Na were compared with apoptotic markers at various times following antineoplastics exposure. Two dyes SBFI/AM (26, 55) and sodium green (3) (Molecular Probes) are used.

a. Sodium green—This dye can be used with flow cytometry. Cell $[Na_i]$ can be determined on selected populations of treated cells. Cells can be sorted based on $[Na_i]$ for subsequent fixation and additional flow cytometry. Sodium green can be used with annexin V by changing to a compatible chromophore (PE) on the annexin and using a propidium iodide substitute (7-AAD) with different fluorescent characteristics (both available from Pharmingen). Then annexin, cell membrane integrity, sodium green fluorescence and forward scattering can be simultaneously determined. To calibrate sodium green, cells are examined while exposed to ionophores (monensin, gramicidin) or a sodium in sensitive dye with similar loading characteristics (e.g. calcein/AM, Molecular Probes).

b. SBFI/AM—This dual excitation wavelength dye is used in a fluorescent plate scanner. With SBFI/AM, we can treat cells cultured in black (non fluorescent) 96 well plates and measure average $[Na_i]$ of the cells in each well. [$Na_i$] is calculated using ratio method and in situ calibration—thus ionophores (monensin and gramidicidin) eliminate the transmembrane gradient so that [$Na_i$] can be altered by changing [$Na_o$].

c. Analysis—Patterns of [$Na_i$] change are examined in relation to events in the apoptotic cascade, and for example, to drug and dose levels, or cell line. Analysis of flow cytometry is performed using standard one and two dimensional histograms and scatter plots.

d. The total cell content of Na can be determined with atomic absorption spectroscopy (AAS) from cell pellets (89) trypsinized from culture dishes.

a. Large cell pellets are obtained from multiple plate cultures (×20 100 mm plates) for each cell line. Total Na per cell and per dry weight of the pellet is obtained in triplicate for each cell population with or without prior treatment.

In vivo Na-MRI studies of human prostate cancer cells propagated as subcutaneous tumors and treated with known antineoplastics—Baseline spectra:

The protocols are constrained by the maximum duration of imaging sessions. Thus a 90 min period of anesthetization during which animals are motionless can readily be attained.

a. Na-MRI images—Control images are acquired for each mouse to be treated. Both single quantum (SQ) and inversion recovery sodium images are acquired. Since they are taken sequentially, they are coregistered.

b. Proton MR images—Proton images are acquired to define the underlying tumor structure.

c. Potential [$Na_i$] gradients associated with inhomogeneous distributions of necrotic tissue, rapidly growing cells (different cell cycle distribution), and non-neoplastic tissues are examined. Some of the larger tumors present with a dark center/bright annulus on the IR image and a bright center on the SQ image, consistent with central necrosis.

d. Analysis/Image intensity is examined as a function of propagating cell line and tumor size, and compared to normal tissue where we expect less intense signal. Line profiles or region of interest analysis will be used to identify the brightest regions of each image. Statistics on the maximum, average pixel intensity, and region area will be examined. Detection of tumors as a function of size (volume), and smallest and largest dimension is examined separately for the different cell lines.

In instances were tumors are to be removed for histological analysis, they are removed from subjects and the alignment of tumor with relation to the field of the main magnet is noted. If cell sodium is known as a function of cell morphology from flow cytometry studies, then planimetry and digital reconstruction of the tumor from histological sections can be used to estimate the 3-dimensional sodium data for comparison with the weighted Na-MR images. This is because equivalent identification of cell morphology can be made for flow cytometry and histology. That is, similar techniques of DNA staining, fluorescent endlabelling, and annexin binding can be used in both modalities.

Chemotherapy as monitored with Na-MRI: Following acquisition of control images, antineoplastics are administered. Mice are reanesthetized and an additional set of MRI images acquired.

Post mortem tumor assays following chemotherapy and imaging: Prior to recovery from the final imaging session, mice are sacrificed, tumors recovered and sectioned. Sections are prepared as follows:

a. Histology—sections are flash frozen or fixed in 10% formalin for later histology and immunohistochemistry as required. In situ fluorescent endlabelling is performed on immunoblanks prepared from fixed tumors by the Cancer Center Molecular Pathology Core.

b. Cultured or fixed for flow cytometry—sections are washed in PBS, treated with collagenase, cultured or fixed for later flow cytometry study. Adequacy of in vivo drug levels are assessed by comparing flow cytometry data of cells from treated tumors versus those cultured directly from commercial stocks.

c. Atomic absorption spectroscopy—sections are blotted and placed in liquid nitrogen for later AAS analysis. For AAS studies, 20 minutes prior to sacrifice, a 100 $\mu$L injection of 80 mM potassium cobaltic EDTA in saline is injected as an extracellular marker into a femoral artery (83, 96). Due to potential problems with inadequate vasculature perfusion, these experiments are performed on small tumors (5–7 mm diameter) where gross evidence of necrosis is not seen, either from histology or in the images. Treated tumors are compared with non-treated controls.

In addition, cells are dissociated from sections of tumor (~0.5 gm ea.) removed from treated and untreated mice. After culturing, they will be subjected to MTT or FACS to look for altered drug response due to in vivo mutations, gene amplification, or altered MDR expression.

Absolute Quantitation (Analyzing Output Signal)

Intensity measurements from user identified image portions are used to determine with definable confidence or to estimate two important clinical and scientific parameters, namely:

[i] average intracellular sodium concentration; and

[ii] percent intracellular volume.

Portions of images means single pixels, groups of pixels determined by categorical groupings or by analysis of local contrast or noise, or regions of interest (defined as collections of pixels with definable boundaries based on properties of variations in the image intensity).

Figure 8A:
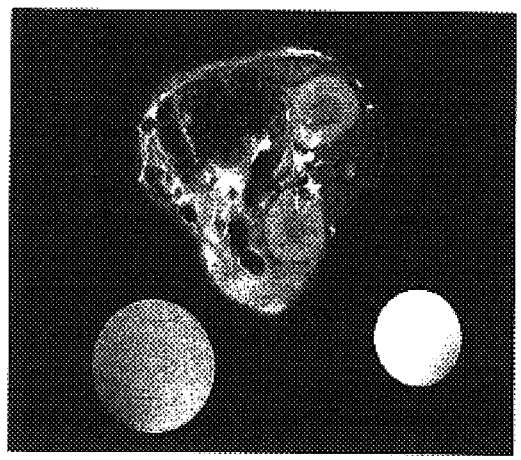
Figure 8A:
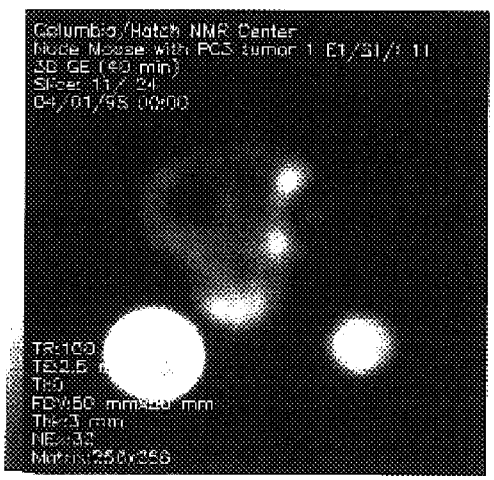
Figure 8A:
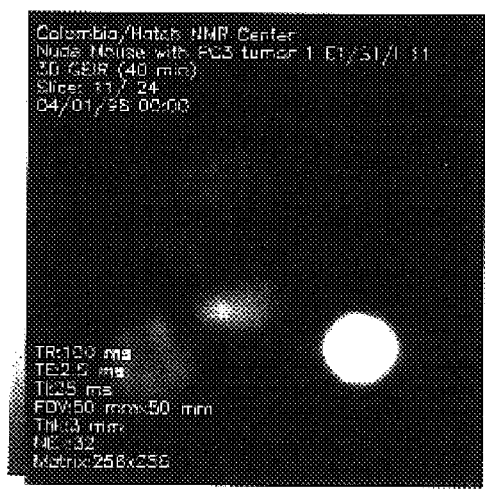
Figure 9:
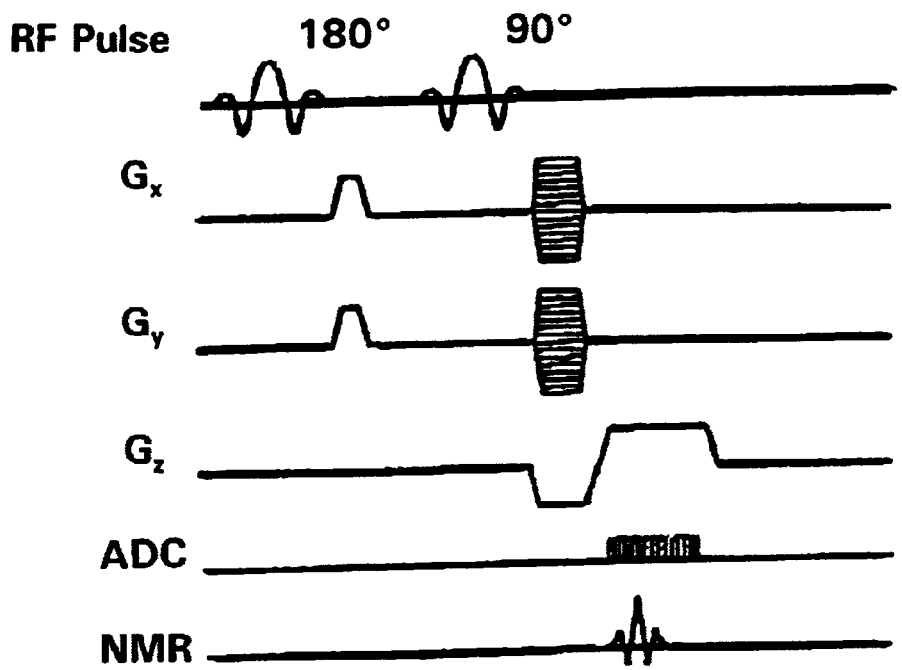
Figure 10:
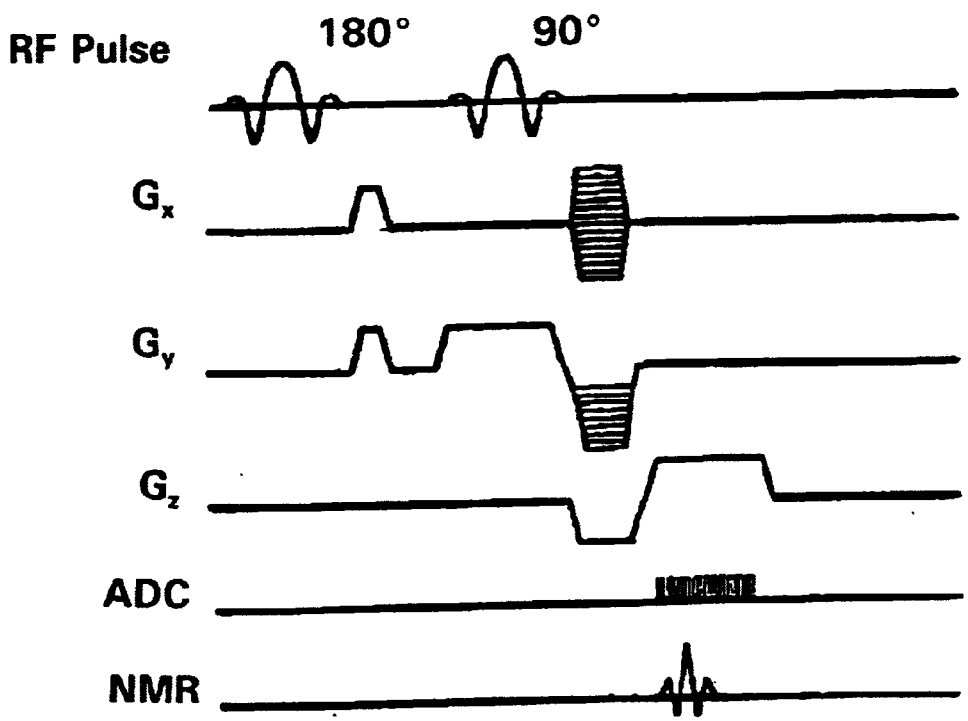
Figure 11:
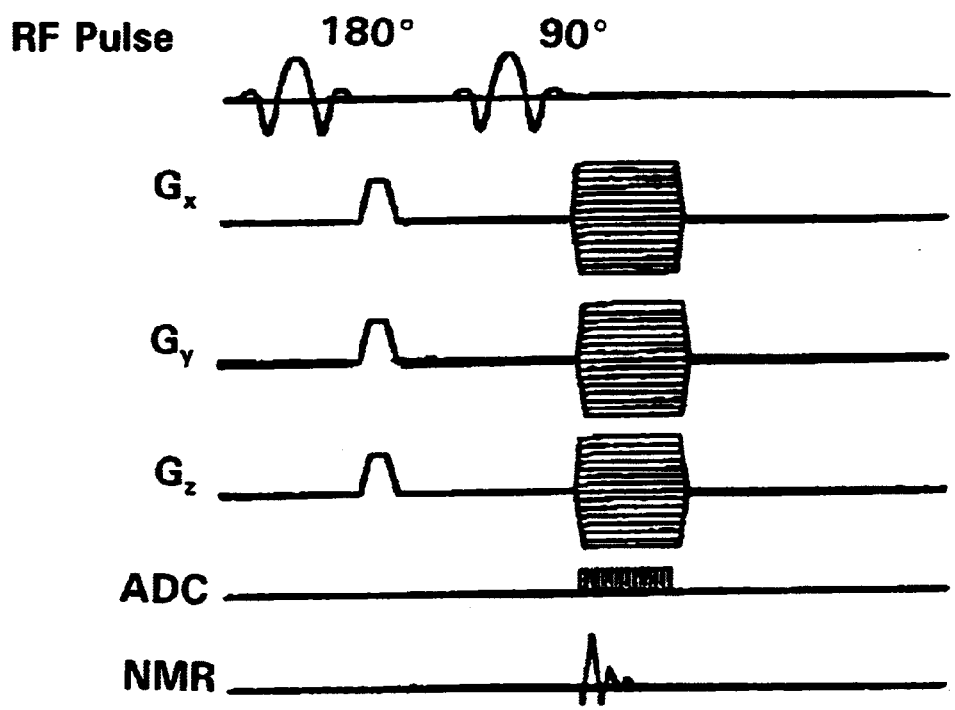
Figure 12:
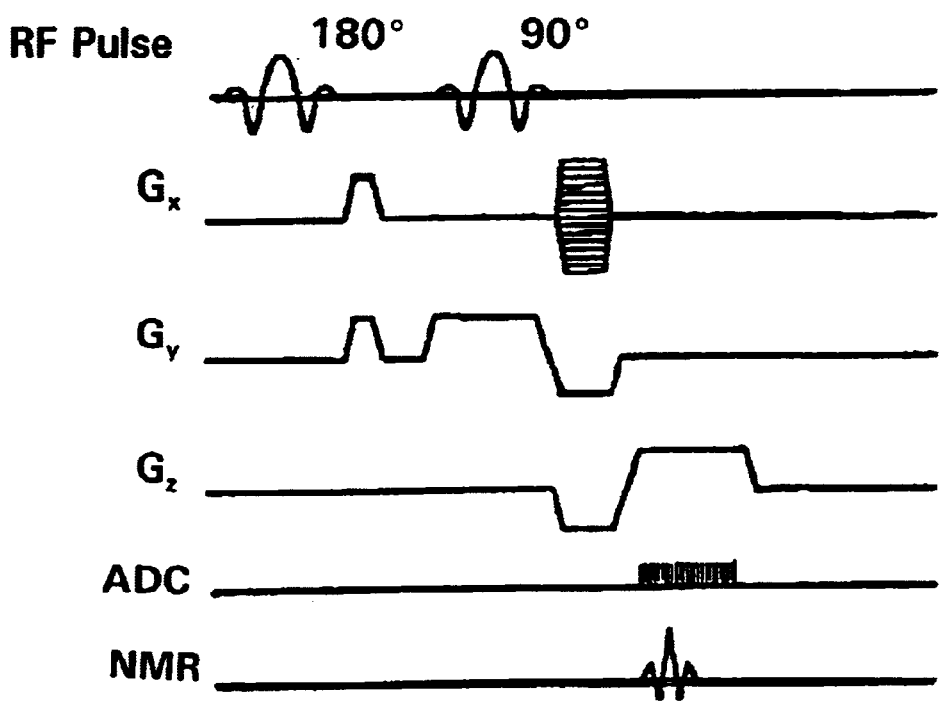
Figure 13:
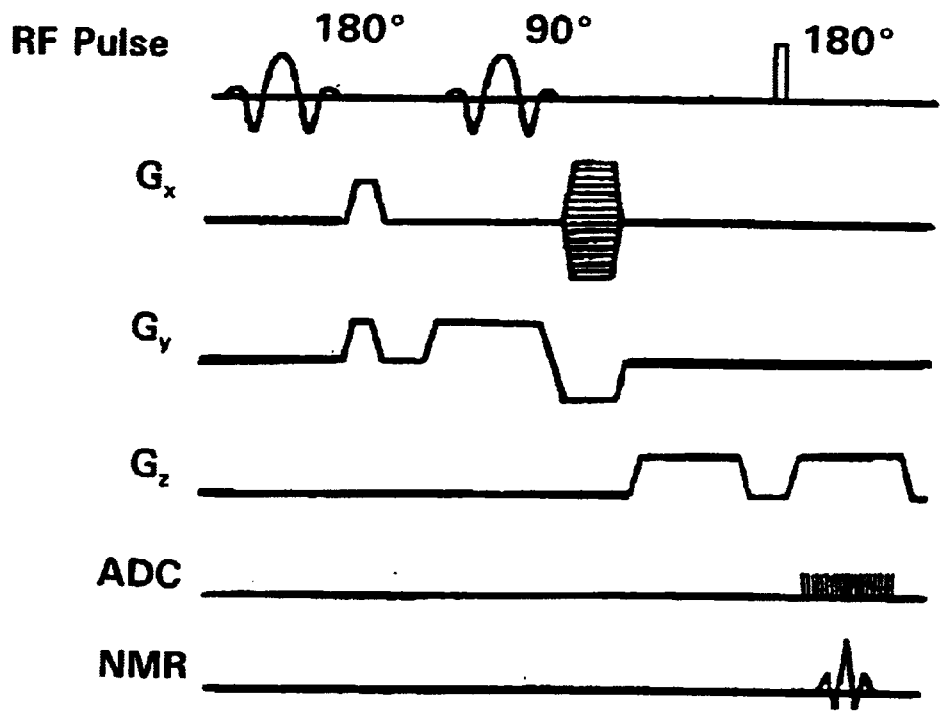
Figure 14:
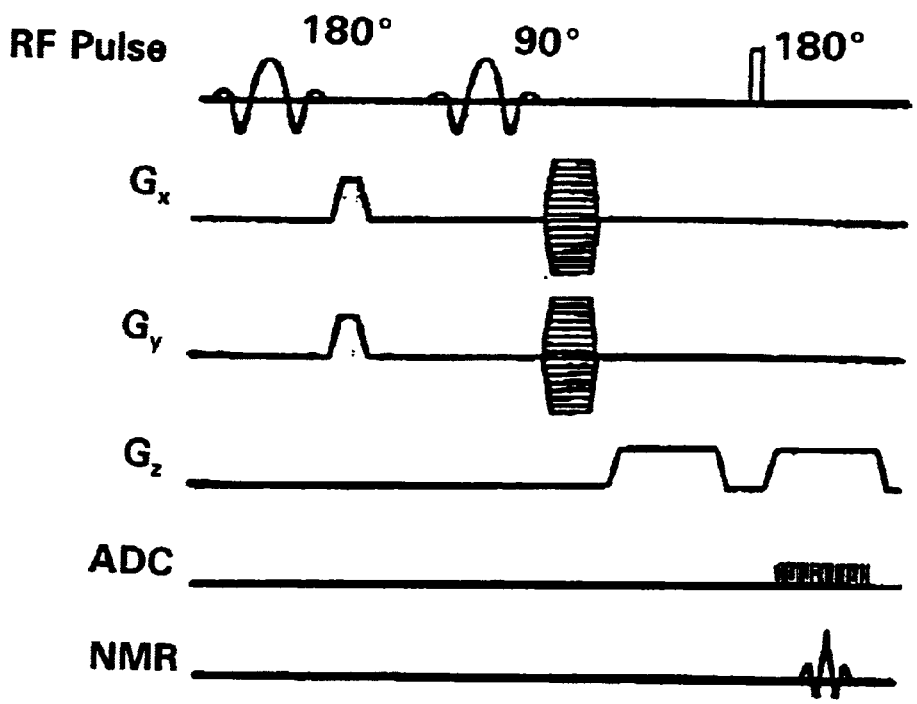

Comparisons over these portions will be made between weighted and unweighted co-registered images. Co-registered images are images using different pulse sequences, but where a pixel to pixel mapping between images identify equivalent physical locations. For the case at hand, experimental animal imaging, two images are co-registered if the images are taken in sequence without the animal moving or the coil positions being changed. Tumor boundary definition will be accomplished with co-registered proton images which show structure. Proton and sodium images can be obtained without changing coils if the coils are doubly tuned. (FIG. 8)

Definitions:

$\Sigma I[a,b]$=integrated image intensity—sum of all pixel intensities over the region defined by the argument 'a' using a pulse sequence defined by the argument 'b'

—where 'a' can range over the following alpha-numeric values and imply:

tum=tumor region bod=body region kid=kidney region phn=phantom region reg=other region defined by pixel addresses or anatomical locations or image areas operationally defined based on contrasts and intensities.

—where 'b' can range over the following alpha-numeric values and imply:

ir(t)=inversion recovery sequence with inversion time 't' in msec.

sq=single quantum sequence

I[a,b]=average image intensity=integrated image intensity/number of pixels=$\Sigma I[a,b]/\#px$ where we define #px as the number of pixels in the regions defined by 'a'.

$V_i$=All volume within cells and within tumor boundary or defined region.

$V_o$=All volume outside cells but within tumor boundary or defined region.

$V_T$=all volume within tumor boundary or within defined region.

$V_i/V_T$=relative intracellular volume.

$C_i$ average intracellular sodium concentration (units of moles of Na nuclei per intracellular volume in liters).

$C_o$ average extracellular sodium concentration (units of Na moles of nuclei per extracellular volume in liters). We approximate $C_o$=145 millimoles per liter (mMol/L), the plasma value since extracellular sodium is relatively constant even in nerve and heart tissue with a large membrane density of gated sodium channels. Average clinical values could be used in place of this estimate. In a contemplated embodiment, plasma sodium levels could be measured for each patient prior to imaging and used for this value. A series of phantoms would be available having been tested and characterized. They would contain values of sodium concentration over the normal expected range varying in steps of 1 mMol/L. Using varying concentrations of Ficoll or agarose, phantoms would also have varying $T_1$ values over an expected range in steps of 1 millisecond (for example, bit not limited to 35 msec to 55 msec). If possible $T_2$ values could also be matched between the phantom and the extracellular fluid, but alternatively they could be measured and difference corrected for by the equation just below for S. Since echo times can be kept short compared to $T_2$, this correction may be small.

Various times In the pulse sequence and sample are given a8: $T_1, T_2, T_R, T_E, T_x$ which are respectively the longitudinal relaxation times 1 and 2, the repetition and echo times, and the time to the inversion pulse.

The composite or average intracellular and extracellular optimum inversion times for maximum suppression are denoted, $T_{x,i}$ and $T_{x,o}$. We refer to the composite intracellular $T_1$ as $T_{1,i}$ and the composite extracellular $T_1$ as $T_{1,o}$.

The equation relating signal attenuation as a result of an inverting pulse is given by:

$$S=N[1-2\exp(-T_I/T_1)+2\exp(-(T_R-T_E/2)/T_1)-\exp(-T_R/T_1)]\exp(-T_E/T_2)$$

where we define $F[T_1, T_2, T_R, T_E, T_I]$ as the attenuation function, which for short $T_E$ and long $T_R$ and $T_2$, can be approximated as $A\ f(T_1, T_I)$. These functions give the relative dependence on the various time constants and pulse sequence intervals. The constant 'N' or 'A' is a function of units, equipment amplification, field strength and others instrumental parameters. Using the selected phantom just described with equation 3 below, 'A' can be determined. This equation can be used to estimate single quantum images without inversion pulses by setting the inversion time=0.

Commercially available software and procedures exist in the public domain to identify tumor regions from proton images and to process image signals to enhance the information content of these images. For the purposes of this disclosure we will illustrate a case whereby the region of Interest is well defined in terms of pixel coordinates and all images referred to are co-registered. We do not limit identification of tumor regions solely to those identified on co-registered proton images, since the several sodium images described can be used separately or together to identify tumors de-novo or to discriminate between tumors and other contrast entities delineated on proton images. We illustrate here the quantitation algorithm in it simplest form whereby the region of interest is defined. Defining the region of interest in the optimum embodiment may require interactive analysis between proton and sodium images.

Given presumably homogenous regions of interest, which for simplicity we refer to as tumor (i.e., a='tum'), we use the following four equations with four unknowns. Two of these unknowns are the intracellular sodium concentration ($C_i$) and the relative intracellular volume ($V_i/V_T$). We assume that the optimal inversion time for suppression of the sodium in extracellular fluid can be estimated by minimizing the IR image of the kidney or a cyst. The third unknown is the composite intracellular $T_i$ (i.e. $T_{1,i}$). If it can not be estimated an additional equation is needed, hence Quantitation Equation 4. In terms of required measurements we need average image intensity from both the single quantum and inversion recovery images, as well as single quantum image values for the phantom defined above. For the case where we must also determine the composite intracellular $T_1$, we need the inversion time which produces the lowest values for the total tumor image intensity.

Quantitation Equation 1: Quantitative estimation of average IR($T_x$) image intensity as a function of relaxation times, inversion times, relative intracellular volume, and intracellular sodium concentration.

$$I[tum,\ ir(T_{x,o})]=(1/\#px)\Sigma I[tum,\ ir(T_{x,o})]=C_o A\ f[T_{1,o},\ T_{x,o}](1-(V_i/V_T))+C_i A\ f[T_{1,i},\ T_{x,o}](V_i/V_T)$$

Quantitation Equation 2: Quantitative estimation of average single quantum image intensity as a function of relaxation times, inversion times, relative intracellular volume, and intracellular sodium concentration.

$$I[tum,\ sq]=I[tum,\ ir(Tx=0)]=(1/\#px)\Sigma I[tum,\ ir(0)]=C_o A\ f[T_{1,c}, 0](1-(V_i/V_T))+C_i A\ f[T_{1,i}, 0](V_i/V_T)$$

Quantitative Equation 3:

$$I[phn,sq]=I[phn,\ ir(0)]=(1/\#px)\Sigma I[phn,\ ir(0)]=C_o A\ f[T_{1,o}, 0](1-(V_i/V_T))+C_i A\ f[T_{1,i}, 0](V_i/V_T)$$

however, since $V_i$=0 for the phantom, the equation becomes:

$$I[phn,\ sq]=C_o A\ f(T_{1,o}, 0)=C_{phn} A\ f(T_{1,phn}, 0)$$

Since $C_{phn}$ and $T_{1,phn}$ are set by design, and the average image intensity is measured for each imaging session, we can calculate the value of 'A' and include it in Quantitation Equations 1 & 2 above.

Quantitation Equation 4: We experimentaly determine the optimum inversion time to lower the total tumor image ($T_{x,min}$, where I[tum, ir($T_{x,min}$)] is a minimum). This $T_{x,min}$ is obtained by differentiating the intensity equation (eqn. #1) in $T_x$, and setting it equal to 0, as follows.

$$dI/dT_x=C_o A(1-(V_i/V_T))df[T_{1,o},\ T_{x,min}]/dT_x+C_i A(V_i/V_T)df[T_{1,i},\ T_{x,min}]/dT_x=0$$

For the Na MRI pulse sequences used here, with repetition times on the order of 100 msecs and spatial resolutions on the order of 1 mm, during the course of a pulse cycle sodium are going to move by diffusion between microscopic domains, or are going to go from being bound to unbound.

This smears the distribution of real $T_1$ values while giving a stable composite $T_1$ which appears well behaved in response to the inversion pulse. Spatial resolution is not a problem since the tumor domains (surviving cells, apoptotic regions, liquification necrosis, coagulation necrosis, and cell free fluid) are sufficiently large to appear in the images.

Discussion

Whereas proton MRI, which uses the hydrogen nucleus, is ideal for structural studies, this invention develops a clinical diagnostic approach using multiple quantum Na-MRI due to the major involvement of Na in important dynamic processes in the cell. Thus sodium free concentration, $[Na_i]$, due to its dependence on metabolic energy for homeostasis and its link to calcium and hydrogen ions through coupled exchangers, is altered in many pathophysiological conditions of clinical interest; and, hence, is an indicator for many types of pathology including malignancy, myocardial ischemia and infarction, arrhythmias, and stroke.

Further, due to its multiple spin state transitions, Na can be examined through specific pulse sequences whereby the contribution of a particular molecular environment may be enhanced. Assessment of efficacy of antineoplastic therapy is clearly a major potential application of this approach since tumors have already been shown to have elevated intracellular sodium and the treatment process itself kills cells which elevate sodium further. Tumors offer the added advantage of being stationary, so they do not independently move as does the heart. Finally, there is substantial clinical motivation for an early assessment of drug efficacy.

Changes in intracellular sodium $[Na_i]$ have been is described in a variety of biological systems during normal and pathophysiological events relevant to chemotherapy including movement throughout the cell cycle, apoptosis, necrosis, metabolic suppression, and transformation from normal to neoplastic tissue. For example during metabolic suppression in heart $[Na_i]$ is elevated and was so measured using multiple quantum MRI in isolated mammalian heart. (20, 20B, 91) $[Na_i]$ changes occur within minutes or hours in response to alterations in transmembrane flux or subcellular sequestration. Therefore, we have delineated a thorough study of both the imaging aspects of Na measurement and interpretation, and the cellular physiology involved with in vitro tissue culture studies.

Flow cytometry was used to examine a second, presumably an earlier event in the apoptotic cascade, reorientation of phosphatidylserine within the cell membrane (FIG. 3.B.). Live cells were exposed to an annexin\V/FITC conjugated antibody. For annexin labeling, cells were cultured for 1 day, treated, then lifted off the culture plate using PBS plus EDTA and exposed to Annexin V/FITC conjugated antibody. Trypsin—which cleaves the antibody binding site—was avoided. Cells were then examined with flow cytometry as per Kit instructions (product #AG604, Chemicon International. (93) Enhanced fluorescence indicates early cellular commitment to the apoptotic cascade. The annexin V response to 10 μg/ml VP-16 etoposide (10 μg/ml) was pronounced at 24 and apparent at 17 hrs, but not at 5 hrs. Up to ⅔ of the live cells (propidium iodide negative) were in the well defined annexin V positive peak (top insert, FIG. 3.B.). The taxotere response was much less pronounced at 24 hrs (10 nM), but was substantially greater at higher drug concentrations (10.0 μM) or at later times (e.g. 48 hrs), where a response comparable to VP16 etoposide occurred. From dose response curves with annexin V fluorescent antibody, we determined that our standard doses were approximately 3×Kd measured at 24 hrs for VP-16 and 48 hrs for taxotere.

Comparison of the latency of these apoptotic markers with the ionic responses induced by taxotere and VP-16 at the same doses (10 nM and 10 ug/ml, respectively). $[Na_i]$ was examined in cultured PC3 cells loaded with the ratiometric fluorescent dye, SBFI/AM (26, 55). Since its dual wavelength ultraviolet excitation requirement is impractical for flow cytometry, adherent cells were examined in 96 well culture plates using a fluorescent plate reader (Titertek, Fluoroskan II). After drug exposure for 2–24 hours, the cells were incubated in dye loading buffer, and then examined using two excitation wavelengths. For fluorescent ion measurements (free $[Na_i]$ and $[Ca_i]$) cells were plated in 96 well, all black, low autofluorescence plates treated for cell culture (Costar). Clear bottom plates were used as controls to visualize parallel cell plating. All wells were run simultaneously, so drug exposure was set by time of drug addition. Following treatment, all wells were washed twice with PBS, then covered with 125 μL of dye loading buffer for 1 hr. For $[Ca_i]$ measurements, 50 μg Fura II/acetoxymethylesther (AM; in 10 μL DMSO) was added with 30 μL pluronic to 6 ml of room temperature, serum free, clear DMEM—, i.e. no pH indicator dye. For $[Na_i]$ measurements, Fura II/AM was replaced by 100 μg SBFI acetoxymethylester (AM) and dye loading of cells was for 3 hrs. (Both dyes and pluronic from Molecular Probes, Eugene, Oreg.). Wells were then washed with PBS, followed by replacement with a measurement buffer (PBS plus 1.0 mM Ca++, 0.6 mM Mg++, and 2 mg/ml dextrose—dye free DMEM had significant autofluorescence). The ratios of emission intensity at the two excitation wavelengths were calculated for each well, and the average ratio plotted for each time point (FIG. 3.C.; left vertical axis). Changes in ratio indicate changes in $[Na_i]$. The mean ratio values increased as early as 2 hours and were statistically significant by 6 hours after exposure to either 10 nM taxotere or 10 μg/ml VP-16 etoposide. The absolute concentration values of the $[Na_i]$ changes were calculated from "in situ" calibration data (FIG. 3.C., right vertical axis) and varied between 10 and 20 mM (16).

Since Ca++ is coupled to Na+ by way of cell and mitochondrial membrane exchangers, and is linked to cell death and apoptosis or cellular dysfunction, free concentration changes in $[Ca_i]$ were expected based on the $[Na_i]$ result. Measuring $[Ca_i]$ with the ratiometric dye, Fura II/AM (73), served as an additional confirmation of ionic response. Dual excitation ratio values were measured in a similar fashion and plotted versus time (FIG. 3.D.; left vertical axis). Early and sustained $[Ca_i]$ elevations were seen, starting at 2–6 hours and continuing to increase in most cases for at least 18 hours. We estimated the average peak $[Ca_i]$ elevation at 150 micromolar (left vertical axis) (73). Due to the high signal to noise of Fura II, we could use lower drug doses, measure $[Ca_i]$ dose response curves, and determine that the Kd for this ionic response at 18 hrs were comparable to that of the annexin response measured at appropriately later times.

The effect of chemotherapy on the IR sodium image intensity in PC3 and DU145 tumors was consistent with the culture results. Control and post-therapy images were acquired in sixteen mice, and tumors in two additional mice had images reacquired following control saline injections. Under observation through a dissection microscope and while the mouse was anesthetized with ketamine and xylazine, one of the two femoral veins was surgically exposed and chemotherapeutic agents slowly injected in a total injection volume less than 150 µL (mouse total circulatory volume is approximately 2.5 ml). We injected 150 µL of 10 mg/ml taxotere (i.e. 1.5 mg) or 100–200 µL of 2 mg/ml VP-16 (0.2–0.4 mg). The reported toxic mouse dose for taxotere is (4.5 mg). These values were calculated from human doses using standard equations which convert weight to surface area for small mammals. Typical human doses per square meter for taxotere and for VP-16 etoposide are respectively 60–100 mg and 100 mg. Tum(rs were removed from animals following the final imaging session, and examined histologically to confirm their cellular constituents.

Tumors were weighed, measured, preserved in 10% formalin, sectioned, and stained with H&E. Most tumors were elliptical in shape and were encapsulated by an endothelial membrane. Beneath an endothelial sheath were cells characterized as high grade carcinoma. Elliptical dimensions of major and minor axes were in the ranges of 1.0–1.5 and 0.5–0.8. Quantitative immunofluorescent studies are required to determine the differential response of chemotherapy versus ambient necrosis. Tumor weights ranged from 230 mg to 1.5 gms. This result is best illustrated visually by showing images from a particular experiment where, in addition to the intensity change, there was a clear spatial broadening of the tumor on the IR image. This is illustrated with two adjacent IR slices from image sets prior to (panels A & B) and subsequent to (panels C & D) taxotere administration (FIG. 5a). Preliminary studies show end labeling fluorescence is brightest in regions suggesting imaging results (5b).

The in vivo injection doses were picked to be comparable to human clinical doses, and were at the high end of the maximum tolerable dose (MTD) range for nude mice. From clinical studies (9B) of plasma levels following human single loading doses of taxotere, peak values were about 5 µMol/L, were in excess of 50 nMol/L for the first 9.6 hrs, and in excess of 10 nMol/L for the first 25 hrs. We have shown that exposure to 10 nMol/L in tissue culture resulted by 6 hrs in significant ionic elevations ($[Na_i]$, $[Ca_i]$), which persisted for at least 24 hrs. Furthermore, this dose of taxotere in culture was sufficient to induce detectable markers for apoptosis by 24 hrs, which by 48 hrs were pronounced. Thus while the apoptotic markers increased progressively for 1–2 days, the ionic activity elevations occurred more rapidly. In vivo effects of chemotherapy were apparent at the earliest measurement time (24 hrs).

However, both doses satisfied the criteria of exceeding the IC50 for exposure times between 24 and 48 hrs. This criteria were used since we planned to do postchemotherapy reimaging studies at 24 and 48 hours, and we needed a large portion of the cell population in vivo to undergo synchronized cell death during this period. Too high or too low a dose is problematic, since there is either no coordinated response, or the cells die and then leave the imageable population.

Consistent with results herein are published results showing a higher ratio of intracellular Na+/K+ in both benign and malignant tumors than in their normal cellular counterparts (57). In various colonic and uterine tissues in vitro, $[Na_i]$ was elevated by as much as a factor of two in neoplastic compared to normal tissue, malignant compared to a benign tumor, and poorly differentiated compared to a well-differentiated tumor (56). Since ionic alterations are important events in malignant transformation, apoptosis and necrosis, it is not surprising that successful antineoplastics affect intracellular ions, and specifically $[Na_i]$. Antineoplastics can change cell cycle distribution often leading to apoptosis, and both changes in cell cycle phase and apoptosis alters $[Na_i]$ (21). Antineoplastics affect various cellular targets which may alter ion activity, including destruction of actin filaments, microtubules, and suppression of protein synthesis and metabolism.

For example, antineoplastics colchicine and lonidamine both increase $[Ca_i]$ and alter its subcellular handling (9, 14). Consistent with the above results, VP-16 etoposide is reported to elevate $[Ca_i]$ and $[Na_i]$, lowers pHi, and decreases $[K_i]$ (7) in L cells. Both lonidamine and VP-16 are reported to cause a net reduction of total cellular monovalent cations, where K+ loss exceeds Na+ gain (7). Furthermore, both Ca++ and H+ levels within cells are controlled by exchangers coupled to the transmembrane Na+ gradient (48); and H+ and Ca+, have both been linked to apoptotis through pHi and $[Ca_i]$ dependent endonucleases, effects on cellular Ca++ buffering and destabilization of the cytoskeleton (21, 98).

Diffusion on a molecular level could result in exchange of sodium between molecular domains with different T1 values during the recovery from the inversion pulse. As has been shown in submicron vacuoles (30), this exchange process could lead to an averaging of the T1 values for the different populations. However, the size of the tumor cells, the slowing of diffusion in the presence of binding sites, and the limited unidirectional exchange through the polarized cell membranes make substantial exchange between sodium in the intracellular and extracellular compartments during an inversion pulse unlikely (48). Measured values of mammalian intracellular and interstitial T1 are consistent with our interpretation of these findings. The T1 for interstitial space or in vitro plasma is ~34 msec, which gives a 25 msec optimal inversion time. At this inversion time, the somewhat smaller estimated intracellular T1 value (23 msec) would suffer a 66% reduction in signal amplitude.

Application of this technique to tumor has several distinct advantages: i) the reduced extracellular matrix structure in tumors due to the release of metalloproteinases which could lower the population of bound extracellular sodium; ii) the higher total sodium in neoplastic versus normal tissue, both due to the increased $[Na_i]$ and to the increased extracellular space volume; iii) the relative stability of intracellular T1 during interventions like hypoxia; and, iv) the marked effect of chemotherapy on processes related to sodium. Furthermore, since the purpose of weighting Na MR images using inversion recovery is to expose the volatile population of sodium nuclei relevant to a major clinical issue. Nevertheless, this is now plausible using algebraic manipulation of single quantum and IR images, or in combination with multiple quantum filters, whereby information from multiple transverse relaxation components are also analyzed.

Whereas proton MRI, which uses the hydrogen nucleus, is ideal for structural studies, we have chosen to develop clinical diagnostic approaches using Na-MRI due to the major involvement of Na in important dynamic processes in the cell, one of which, illustrated here, is interaction of chemotherapy, cellular apoptosis and ions.

REFERENCES

1. Adams, D. A., et al. (1985) "Radioimunotheraphy of human lymphoma in athymic, nude mice as monitored by $^{31}$P nuclear magnetic resonance", *Biochem & Biophys Res Commun*, 131(2):1020–1027;
2. Alli, J. L., et al. (1991) "Absolute qualification of intracellular Na=using triple quantum-filtered sodium-23 NMR", *J Mag Reson*, 93:71–76;

3. Amorino, G. P. and Fox, M. H. (1995) "Intracellular Na+ measurements using sodium green tetra-acetate with flow cytometry", *Cytometry*, 21:248–256;
4. Balschi, J. A. et al. (1990) "31P and 23Na NMR spectroscopy of normal and ischemic rat skeletal muscle. Use of shift reagent in vivo", *NMR in Biomedicine*, 3(2):47–58;
5. Balschi, J. A., et al. (1982) "Direct high-resolution nuclear magnetic resonance studies of cation transport in vivo: Na+ transport in yeast cells", *Biophys J*, 38:323–3276;
6. Bansal, G., et al. (1992) "In vivo Na-23 MR imaging and spectroscopy of rat brain during Tm(DOTP)5-infusion", *J Magn Reson Imag*, 4:385–391;
7. Barbiero, G., et al. (1995) "Intracellular ionic variations in the apoptotic death of L cells by inhibitors of cell cycle progression", *Experimental Cell Res.*, 217:410–418;
8. Berendsen, H. J. C. and Edzes, H. T. (1973) "The observation and general interpretation of sodium magnetic resonance in biological material", *Ann NY Acad Sci*, 104:455–585;
9. Bonfoco, E., et al. (1995) "Colchicine induces apoptosis in cerebellar granule cells", *Experimental Cell Research*, 218(1):189–200;
9B. Bruno, R., et al. (1998) "Population pharmacokinetics/pharmacodynamis of docetaxel in phase II studies of patients with cancer. *J Clin Onco*, 16(1):187–196;
10. Bull, T. E. (1972) "Nonexponential relaxation of 23Na in agarose gels", *J Magn Reson*, 8:344–353;
11. Buster, D. C., et al. (1990) "23Na shift reagent for perfused rat hearts", *Magn Reson Med*, 15:25–32;
12. Butwell, N. B. et al. (1991) "Influence of cardiac pacing on intracellular sodium in the isolated perfused rat heart", *Invest Radiol*, 26:1079–1082;
13. Cameron, I. L., et al. (1980) "Intracellular concentration of sodium and other elements as related to mitogenesis and oncogenesis in vivo", *Cancer Res*, 40:1493–1500;
14. Castiglione, S., et al. (1993) "Non-ionophoretic elevation of intracellular Ca++ by Lonidamine", *Biochem Pharm*, 46(2) 330–332;
15. Cohen, I. S., et al. (1989) "Repetitive activity: origin of Na+ load and its physiologic effects. In: Lethal Arrhythmias Resulting from Myocardial Ischemia arid Infarction", M. R. Rosen, Y. Palti (eds), Kluwer Academic Publishers, Boston/Dordrecht/London, 31–40;
16. Cohen, I. S., et al. (1987) "Models of the Na/K pump in cardiac muscle predict the wrong intracellular Na+ activity", *Proc Roy Soc Lond (B)*, 231:371–382;
17. Columbano, A. (1995) "Cell Death: current difficulties in discriminating apoptosis from necrosis in the context of pathological processes in vivo", *J Cell Biochem*, 58:181–190;
18. Cockman, M. D., et al. (1990) "Double-quantum-filtered sodium imaging", *J Magn Reson*, 90:9–18;
19. Darzynkiewicz, Z., et al. (1992) "Features of apoptotic cells measured by flow cytometry", *Cytometry*, 13:795–808;
20. Dizon, J., et al. (1996) "Evaluation of triple-quantum filtered Na NMR monitoring of intracellular Na content in the perfused rat heart: Comparison of intra- and extracellular transverse relaxation and spectral amplitudes", *Magn Reson Med*, 35:336;
20B. Dizon, J., et al. (1998) "Metabolic inhibition in the perfused rat heart: evidence for glycolytic requirement for normal sodium hmeostasis", *Am J Physiol*, 274:1082;
21. Elledge, S. J. (1996) "Checkpoints: preventing an identity crisis", *Science*, 274:1664–1671;
22. Goldberg, G. I. and Eisen, A. Z. (1991) "Extracellular matrix metalloproteinases in tumor invasion and metastasis", *Cancer Treat Res*, 53:421;
23. Gorczyca, W., et al. (1993) "Detection of DNA strand breaks in individual apoptotic cells by the in situ terminal deoxynucleotidyl transferase and nick translation assays", *Cancer Research*, 53:1945–1951;
24. Gullapalli, R. P., et al. (1992) "Effect of lithium on the double-quantum behavior of 23Na in normal human erythrocytes", *Magn Reson Med*, 27:1–12;
25. Gupta, R. K. and Gupta, P. (1982) "Direct observation of resolved resonances from intra-and extracellular sodium-23 ions in NMR studies of intact cells and tissues using dysprosium (III) tripolyphosphate as a paramagnetic shift reagent", *J Magnn Reson*, 47: 344–350;
26. Harootunian, A. T., et al. (1991) "Fluorescence ratio imaging of cytosolic free Na in individual fibroblasts and lymphocytes", *J Biol Chem*, 264:19458–19467;
27. Hubbard, P. S., et al. (1970) "Non-exponential nuclear magnetic relaxation by quadruple interactions",*J Chem Phys*, 53(3):935–937;
28. Hutchinsen, R. B., et al. (1993) "Changes in double-quantum filtered sodium intensity during prolonged ischemia in the isolated perfused heart", *Magn Reson Med*, 29:391–395;
29. Hutchinsen, R. B., et al. (1990) "Evaluation of the double-quantum filter for the measurement of intracellular sodium concentration", *J Biol Chem*, 53(3): 985–987;
30. Jaccard, G., et al. (1970) "Multiple-quantum NMR spectroscopy of S=3/2 spins in isotropic phase: a new probe for multi-exponential relaxation", *J Chem Phys*, 53(3):985–987;
31. Jelicks, L. A. and Gupta, R. K. (1989) "Observation of intracellular sodium ions by double-quantum filtered 23Na NMR with paramagnetic quenching of extracellular coherence by gadolinium tripolyphosphate", *J Magnn Reson*, 83:146–151;
32. Jelicks, L. A. and Gupta, R. K. (1989) "Double-quantum NMR of sodium Lons in cells and tissues. Paramagnetic quenching of extracellular coherence", *J Magn Reson*, 81:586–592;
33. Jelicks, L. A. and Gupta, R. K. (1989) "Multinuclear NMR studies of the Langendorf perfused rat heart", *J Biol Chem*, 264:15230–15235;
34. Jelicks, L. A. and Gupta, R. K. (1994) "Nuclear magnetic resonance measurement of intracellular sodium in the perfused normotensive and spontaneously hypertensive rat heart", *Am J Hypertension*, 7:429–435;
35. Jiang, T., et al. (1996) "Endothelin-dependent actions in cultured AT-1 cardiac myocytes: the role of the epsilon-isoform of protein kinase", *C Cir Res*, 78(4):1–13;
36. Jiang, T., et al. (1996) "Abnormal calcium regulation in hypertrophied atrial tumor myocytes (AT-1 cells)", *Circulation*, 94:I663;

37. Jung, K. J., et al. (1996) "New double quantum filtering schemes", *J. Magn. Reson B.*, 112:214227;

38. Jung, K. J., et al. (1996) "Chemical-shift-selective (CSS) acquisition of multiple-quantum (MQ) 23Na signal", *J Mag Reson*, 112:214–227;

39. Jung, K. J., et al. (1995) "Breakthrough of single-quantum coherence and its elimination in double-quantum filtering", *J Magn Reson*, 107: 235–241;

40. Jung, K. J. and Katz, J. (1996) "Mathematical analysis of single-quantum breakthrough due to intersequence stimulated echo in double quantum filtering (DQF)", *J Magnn Reson*, 124:232–236;

41. Jung, K. J. and Katz, J. (1996) "Measurement of biexponential transverse relaxation times from phantoms simulating 23Na in biological systems using multiple-quantum (MQ) filtering", *Soc Magn Reson*, 1173;

42. Jung, K. J., et al. (1997) "Quantitative study of intracellular and extracellular Na in biological systems using multiple-quantum filtering in the absence of shift reagents", *Soc Maag Reson Med*, 486;

43. Jung, K. J., et al. (1997) "Measurement of transverse relaxation times and content ratio of 23Na in phantoms simulating biological systems by use of multiple-quantum filtering", *J Magnn Reson*, 124:393–399;

44. Karczmar, G. S., et al. (1991) "P-31 spectroscopy study of response of superficial human tumors to therapy", *Radiology*, 179:149–153;

45. Katz J. and Cannon P. J. (1992) "In Cardiac Imaging: A Companion to Braunwald's Heart Disease", M. L. Marcus , D. J. Skorton, M. Schelbert, and G. L. Wolf, Eds. (Saunders Publishing Company, Philadelphia, 828–840;

46. Keller, A. M., et al. (1989) "Sodium invisibility in magnetic resonance spectroscopy: significant differences between single and double-quantum filtered acquisitions", *Book of Abstracts, Soc Magn Reson Med*, 2:502;

47. King, K. L. and Cidlowski, J. A. (1995) "Cell cycle and apoptosis: common pathways to life and death", *J Cell Biochem*, 58:175–180;

48. Kline, R. P., et al. (1990) "Interaction of intracellular buffering with transmembrane coupled ion transport", *J Gen Physiol*, 95:499–522;

49. Kline, R. P., et al. (1993) "Spontaneous activity in transgenic mouse heart: comparison of primary atrial tumor with cultured proliferating AT-1 atrial myocytes", *J Gen Physiol*, 95:499–522;

50. Kline, R. P., et al. (1996) "Immortalized cardiac myocytes undergo hypertrophy in response to cell cycle arrest and retain ability to undergo apoptosis", *Circulation*, 94:166;

51. Koch, K. S. and Leffert, H. L. (1979) "Increased sodium ion influx is necessay to initiate rat hepatocyte proliferation", *Cell* 18:153–163;

52. Koutcher, J. A., et al. (1990) "P-31 NMR spectra of extremity sarcomas:diversity of metabolic profiles and changes in response to chemotherapy", *Magn Reson Med*, 16:19–34;

53. Kruman II, et al. (192) "Apoptosis of murine BW 5147 Thymoma cells induced by cold shock", *J Cell Physioloy*, 153:112–117;

54. Lannigan, D. A. and Knauf, P. A. (1984) "Decreased intracellular Na+ concentration is an early event in murine erythroleulemic cell differentiation", *J Bioll Chem*, 260 (12):7322–7324;

55. Levi, A. J., et al. 1994) "Properties of the fluorescent sodium indicator "SBFI" in rat and rabbit cardiac myocytes", *J Cardioy Electrophys*, 5:241–257;

56. Liebling, M. S. and Gupta, R. K. (1987) "A comparison of intracellular sodium ion concentrations in neoplastic and nonneoplastic human tissue using 23Na NMR spectroscopy", *Ann NY Acad Sci*, 508:149–163;

57. Lukacs, G. I., et al. (1983) "Microfluorimetric and x-ray microanalysis studies on the DNA content and Na+/K+ ratios of the cell nuclei in various types of thyroid tumors", *J Cancer Res Clin Oncol*, 105:280–284;

58. Malloy, C. R., et al. (1990) "Influence of global ischemia on intracellular sodium in the perfused rat heart", *Magn Reson Med*, 15:33–44;

59. Malorni, W., et al. (1992) "The cytoskeleton as a subcellular target of the antineoplastic drug lonidamine", *Anticancer Res*, 12:2037–2046;

60. Marin, M. C., et al. (1996) "Apoptosis suppression by bcl-2 is correlated with the regulation of nuclear and cytosolic $Ca^-$", *Oncocene* 12:2259–2266;

61. Martin, S. J., et al. (1995) "Early redistribution of plasma membrane phosphatidylserine is a general feature of apoptosis regardless of the initiating stimulus: inhibition of overexpression of Bcl-2 and AB1", *Experimental Medicine*, 182:1545–1556;

62. Miller, J. R., et al. (1996) "High temperature superconducting receiver coils for sodium imaging", *IEE Trans on Biomed Enaineerina Reson*, 43:1197–1199;

63. Murphy, A. E., et al. (1996) "Bcl-2 potentiates the maximal calcium uptake capacity of neural cell mitochondria", *Neurobiology*, 93:9893–9898;

64. Nagy, P., et al. (1995) "Ion channel activities regulate transmembrane signaling in thymocyte apoptosis and T-cell activation", *Immunology Letters*, 44:91–95;

65. Naik, H. R., et al. (1995) "Preclinical studies of gossypol in prostrate carcinoma", *Int J Oncology*, 6:209–215;

66. Navon, G. (1993) "Complete elimination of the extracellular 23Na NMR signal in triple quantum filtered spectra of rat hearts in the presence of shift reagents", *Magn Reson Med*, 30:503;

67. Osbakken, M., et al. (1992) "Isolated cardiomyocytes in conjunction with NMR spectroscopy techniques to study metabolism and ion flux", *J Biol Chem*, 267(22):15340–15347;

68. Oudard, S., et al. (1995) "Mitochondria-bound hexokinase as target for therapy of malignant gliomas", *Int J Cancer*, 62:216–222;

69. Payne, G. S. and Styles, P. (1991) "Multiple-quantum filtered 23Na NMR spectroscopy in model systems", *J Magnn Reson*, 95:253–266;

70. Payne, G.S. and Seymour, A M L (1990) "Multiple-quantum filtered 23Na NMR spectroscopy in the perfused heart", *NMR in Biomedicine*, 3(3):139–146;

71. Pekar, J. And Leigh, J. S. (1986) "Detection of biexponential relaxation in sodium-23 facilitated by double-quantum filtering", *Magn Reson*, 69:582–584;

72. Pekar, J., et al. (1987) "selective detection of intracellular sodium by coherence-transfer NMR", *J Magnn Reson*, 72:159–161;

73. Petr, M. J. and Wurster, R. D. (1997) "Determination of in situ dissociation constant for Fura-2 and quantitation of background fluorescence in astrocyte cell line", *Cell Calcium*, 21(3):233–240;
74. Pike, M. M. and Springer, C. S. (1982) "Aqueous shift reagents for high-resolution cationic nuclear magnetic resonance", *J Magn Reson*, 46:348–353;
75. Prescott, D. M., et al. (1993) "Therapy monitoring in human and canine soft tissue sarcomas using magnetic resonance imaging and spectroscopy", *Int J Radiat Biol Oncol Phys*, 28:415–423;
76. Redmon, O. M., et al. (1992) "Osteosarcoma: use of MR imaging and MR spectroscopy in clinical decision making", *Radiology*, 172:811–815;
77. Redmon, O. M., et al. (1992) "P-31 MRS as an early prognostic indicator of patient reponse to chemotheraphy", *Magn Reson Med*, 25:30–34;
78. Redmon, O. M., et al. (1992) "Tissue characterization and assessment of preoperative chemotherapeutic response in musculoskeletal tumors by in vivo P-31 magnetic resonance spectroscopy", *Magn Reson Med*, 27:226–237;
79. Rick, R. (1989) "Electron microprobe analysis of cell sodium in epithelia", *Curr Top Membr*, 34:61–82;
80. Rooney, W. D., et al. (1988) "Two dimensional double-quantum NMR spectroscopy of isolated spin 3/2 systems: 23Na examples", *J Am Chem Soc*, 110:674–681;
81. Rooney, W. D. and Springer, C. S. Jr. (1991) The molecular environment of intracellular sodium: 23Na NMR relaxation", *NMR in Biomedicine*, 4:227–245;
82. Rooney, W. D. and Springer, C. S. Jr. (1991) "A comprehensive approach to the analysis and interpretation of the resonances of spins 3/2 from living systems", *NMR in Biomedicine*, 4:209–226;
83. Scheaffer, E. and Peters, T. (1987) "Determination of the extracellular space with nonradioactive Co3+ EDTA and simultaneous estimation of Na, K, Ca and Mg content in isolated guinea-pig heart preparations by atomic absorption spectroscopy", *Basic REs in Cardiol*, 82:341–347;
84. Schilling, A., et al. (1992) "Liver tumors: follow-up with P-31 MR spectroscopy after local chemotheraphy and chemoembolization", *Radiology*, 182:887–890;
84a. Schultz, P. K., et al. (1995) "Neoadjuvant chemotherapy for invasive bladder cancer: prognostic factors for survival of patients treated with M-VAC with 5 year follow up", *J Clin Onc*, 13:300–302;
85. Seo, Y., et al. (1990) "Measurement of intracellular Na in the rat salivary gland: a 23Na NMR study using double-quantum filtering", *Biochem Biophys Acta*, 1034:142–147;
86. Shinar, H., et al. (1993) "Sodium interaction with ordered structures in mammalian red blood cells detected by Na-23 double-quantum NMR", *Biophys J*, 64:1273–1279;
87. Sorce, D. J. and Katz, J. (1991) "Multiple-quantum filters of arbitrary phases for spin 3/2 nuclei", *Mol Phys*, 80(5):1067–1076;
88. Sorce, D. J., et al. (1993) "Multiple-quantum filters of arbitrary phases for spin 3/2 nuclei," *Mol. Phys.*, 80(5): 1067–1076;
89. Sung, S-S. J., et al. (1985) "Extracellular ATP perturbs transmembrane ion fluxes, elevates cytosolic [C++], and inhibits phagocytosis in mouse macrophages", *J Biol Chem*, 260(25):134421–3449;

90. Tauskela, J. S. and Shoubridge, E. A. (1993) "Response of the 23Na NMR double-quantum filtered signal to changes in Na+ ion concentration in model biological solutions and human erythrocytes", *Biophys Acta*, 1158:155–165;
91. Tauskela, J. S., et al. (1997) "Evalution of multiple quantum filtered Na NMR in monitoring intracellular Na content in the perfused rat heart in the absence of a chemical shift reagent" *J Magn Reson*, 124:232;
92. Tauskela, J. S., et al. (1995) "Detection of an extracellular contribution from a second-rank tensor to the double-quantum 23Na NMR signal in the isolated perfused rat heart", *J Magn Reson*, 108:165–169;
93. Vermes, I., et al. (1995) "A novel assay for apoptosis: flow cytometric detection of phophatidylserine expression on early apoptotic cells using fluorescein labeled Annexin V.", *Immunological Methods*, 184:39–51;
94. Wahl, R. L. et al. (1993) "Metabolic monitoring of breast cancer chemohormonotheraphy using positron emission tomography", *J Clin Oncol*, 11:2101;
95. Whang, J., et al. (1994) "Multiple-quantum filtered NMR determination of equilibrium magnetization for 23Na quantitation in model phantoms", *J Magn Reson B*, 103:175–179;
96. Xia, Z., et al. (1996) "Effects of ischemia on intracellular sodium and phosphates in the in vivo rat liver", *J Applied Physiol*, 81(3):1395–1403;
97. Xn, Li, et al. (1995, "Single-step procedure for labeling DNA strand breaks with fluorescein or BODILY conjugated deoxynucleotides: detection of apoptosis and bromoaeoxyuridine incorporation", *Cytometry*, 20:172–180;
98. Zhu, W. H. and Loh, T. T. (1995) "Effects of Na+/H+ antiport and intracellular pH in the regulation of HL-60 cell apoptosis", *Biochimica et Biophysica Acta*, 1269:122–128;
99. Zs-Nagy, I., et al. (1983) "Correlation of malignancy with intracellular Na:K ratio in human thyroid tumors", *Cancer Res*, 43:5395–5402;

What is claimed is:

1. A method for measuring the magnetic resonance signal of an intracellular population of predetermined nuclei in a cell-containing sample comprising:

(a) applying to the sample a first radio frequency pulse, in a magnetic field, sufficient to cause alignment of the predetermined nuclei within the sample;

(b) after a set time interval ($T_f$), applying to the sample a second radio frequency pulse, in a magnetic field, sufficient to cause a measurable signal in the plane transverse to the direction of nuclear alignment in step (a);

(c) suppressing the measurable signal in the transverse plane attributable to the extracellular population of predetermined nuclei in the sample; and (d) applying image encoding techniques for acquisition of the measurable signal attributable to the intracellular population of predetermined nuclei in the sample, (e) detecting and analyzing the measurable signal to obtain a weighted image;

(f) obtaining an unweighted image of the measurable signal; and (g) comparing the weighted image to the unweighted image of the measurable signal, so as to thereby measure the magnetic resonance signal of the intracellular population of predetermined nuclei in the sample.

2. The method of claim 1, wherein the magnetic field strength is 1 to 15 tesla.

3. The method of claim 1, wherein the magnetic field strength is 1 to 5 tesla.

4. The method of claim 1, wherein the magnetic field is generated by a magnetic coil having a field strength of 4.23 tesla.

5. The method of claim 4, wherein the magnetic coil is tuned for sodium.

6. The method of claim 5, wherein the magnetic coil is multiple-tuned.

7. The method of claim 4, wherein $T_I$ is 25 msec.

8. The method of claim 1, wherein the set time interval $(T_I)$ alone permits suppression of the measurable signal attributable to the extracellular nuclei.

9. The method of claim 8, wherein suppressing the measurable signal comprises minimizing such signal.

10. The method of claim 8, wherein suppressing the measurable signal attributable to the extracellular nuclei comprises the use of phantoms.

11. The method of claim 8, wherein the first pulse is 180°, and the second pulse is 90°, and $(T_I)$ is $(\ln 2)T_1$.

12. The method of claim 1, wherein the predetermined nuclei are sodium nuclei.

13. The method of claim 1, whereby the intracellular and extracellular populations of predetermined nuclei have different longitudinal relaxation times.

14. The method of claim 1, wherein the weighted image and the unweighted image are compared pixel to pixel.

15. The method of claim 1, wherein the weighted image and the unweighted image are compared region to region.

16. The method of claim 1, wherein the weighted image and the unweighted image are compared algebraically.

17. The method of claim 1, wherein the sample is in a subject.

18. The method of claim 17, wherein the subject is a mammal.

19. In The method of claim 18, wherein the subject is a human.

20. The method of claim 1, wherein step (c) is achieved by selecting a suitable $(T_I)$.

21. The method of claim 1, wherein step (c) is achieved by applying a multiple quantum filter.

22. A method for determining the effectiveness of chemotherapy using a chemotherapeutic agent in a subject afflicted with a cancerous tumor comprising:

(a) measuring, according to the method of claim 1, the magnetic resonance signal of an intracellular predetermined nuclei population in a subject to whom the chemotherapeutic agent has been administered; and (b) comparing the signal so measured with a standard, so as to thereby determine the effectiveness of the chemotherapy in the subject.

23. The method of claim 22, wherein the subject is a mammal.

24. The method of claim 23, wherein the mammal is a human.

25. The method of claim 22, wherein the chemotherapeutic agent is administered via intravenous injection, infusion, liposome-mediated delivery, topical, nasal, oral, anal, ocular or otic delivery.

26. The method of claim 22, wherein the cancerous tumor is a prostate or breast tumor.

27. A method for detecting and characterizing a tumor in a sample comprising:

(a) measuring, according to the method of claim 1, the magnetic resonance signal of an intracellular predetermined nuclei population in the sample; and (b) comparing the signal so measured with a standard, so as to thereby detect and characterize a tumor in the sample.

28. The method of claim 27, wherein the tumor is cancerous.

29. The method of claim 27, wherein the sample is in a subject.

30. The method of claim 29, wherein the subject is a mammal.

31. The method of claim 30, wherein the subject is a human.

32. A method for detecting cell death in a cell-containing sample comprising:

(a) measuring, according to the method of claim 1, the magnetic resonance signal of an intracellular predetermined nuclei population in the sample; and (b) comparing the signal so measured with a standard, so as to thereby detect cell death in the sample.

33. The method of claim 32, wherein the sample is in a subject.

34. The method of claim 33, wherein the subject is a mammal.

35. The method of claim 34, wherein the subject is a human.

36. The method of claim 1, wherein the first radio frequency pulse is 180° and the second radio frequency pulse is 90°.

37. The method of claim 1, wherein the image acquired is a two-dimensional image or three dimensional image.

* * * * *